United States Patent
Prieur

(10) Patent No.: US 11,561,225 B2
(45) Date of Patent: Jan. 24, 2023

(54) COMPOSITIONS AND METHODS FOR TREATING LUNG CANCER

(71) Applicant: Progastrine et Cancers S.à r.l., Luxembourg (LU)

(72) Inventor: Alexandre Prieur, Montpellier (FR)

(73) Assignee: Progastrine et Cancers S.à r.l., Luxembourg (LU)

(*) Notice: Subject to any disclaimer, the term of this patent is extended or adjusted under 35 U.S.C. 154(b) by 510 days.

(21) Appl. No.: 16/498,577

(22) PCT Filed: Mar. 30, 2018

(86) PCT No.: PCT/EP2018/058346
§ 371 (c)(1),
(2) Date: Sep. 27, 2019

(87) PCT Pub. No.: WO2018/178364
PCT Pub. Date: Oct. 4, 2018

(65) Prior Publication Data
US 2021/0085784 A1    Mar. 25, 2021

(30) Foreign Application Priority Data
Mar. 30, 2017  (EP) .................................. 17305382

(51) Int. Cl.
| | | |
|---|---|---|
| *G01N 33/574* | (2006.01) | |
| *C07K 16/22* | (2006.01) | |
| *A61P 35/00* | (2006.01) | |
| *A61K 39/395* | (2006.01) | |
| *A61K 45/06* | (2006.01) | |
| *C07K 16/26* | (2006.01) | |
| *C07K 16/30* | (2006.01) | |
| *C07K 16/32* | (2006.01) | |

(52) U.S. Cl.
CPC ... *G01N 33/57423* (2013.01); *A61K 39/3955* (2013.01); *A61K 39/39558* (2013.01); *A61K 45/06* (2013.01); *A61P 35/00* (2018.01); *C07K 16/22* (2013.01); *C07K 16/26* (2013.01); *C07K 16/3023* (2013.01); *C07K 16/32* (2013.01); *C07K 2317/22* (2013.01); *C07K 2317/24* (2013.01); *C07K 2317/34* (2013.01); *C07K 2317/51* (2013.01); *C07K 2317/515* (2013.01); *C07K 2317/565* (2013.01); *C07K 2317/569* (2013.01); *C07K 2317/76* (2013.01); *G01N 2333/595* (2013.01)

(58) Field of Classification Search
CPC .......... G01N 33/57423; A61K 39/3955; A61K 45/06; C07K 16/22
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,975,278 A | 12/1990 | Senter et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,693,761 A | 12/1997 | Queen et al. |
| 5,814,318 A | 9/1998 | Lonberg et al. |
| 5,877,293 A | 3/1999 | Adair et al. |
| 5,886,152 A | 3/1999 | Nakatani et al. |
| 6,054,297 A | 4/2000 | Carter et al. |
| 6,180,370 B1 | 1/2001 | Queen et al. |
| 9,611,320 B2 * | 4/2017 | Pannequin .............. C07K 16/26 |
| 2010/0291193 A1 * | 11/2010 | Singh ...................... A61P 35/00 435/375 |

FOREIGN PATENT DOCUMENTS

| | | |
|---|---|---|
| EP | 0 451 261 B1 | 9/1993 |
| EP | 0 682 040 B1 | 8/1999 |
| EP | 0 566 647 B1 | 10/2003 |
| EP | 1 391 213 A1 | 2/2004 |
| EP | 0 592 106 B1 | 11/2004 |
| EP | 0 519 596 B1 | 2/2005 |
| EP | 0 939 127 B1 | 9/2014 |
| WO | WO 91/10741 A1 | 7/1991 |
| WO | WO 94/11026 | 5/1994 |
| WO | WO 96/33735 A1 | 10/1996 |
| WO | WO 96/34096 A1 | 10/1996 |
| WO | WO 98/16654 A1 | 4/1998 |
| WO | WO 98/24893 A2 | 6/1998 |
| WO | WO 98/46645 A2 | 10/1998 |
| WO | WO 98/50433 A2 | 11/1998 |

(Continued)

OTHER PUBLICATIONS

Fluorouracil, retrieved from https://www.cancerresearchuk.org/about-cancer/cancer-in-general/treatment/cancer-drugs/drugs/fluorouracil on Apr. 1, 2022 (Year: 2022).*

Sunshine et al., PD-1/PD-L1 inhibitors, Current Opinion in Pharmacology, 2015, 23:32-38, Publication Date: Jun. 2, 2015 (Year: 2015).*

Almagro & Fransson, Humanization of antibodies, Frontiers in Bioscience 2008; 13: 1619-33 (Year: 2008).*

Chan et al., *Targeted therapy for non-small cell lung cancer: current standards and the promise of the future*, 4(1) Translational Lung Cancer Research 36-54 (2015).

(Continued)

*Primary Examiner* — Peter J Reddig
*Assistant Examiner* — Cheng Lu
(74) *Attorney, Agent, or Firm* — Panitch Schwarze Belisario & Nadel LLP; Erin M. Dunston

(57) ABSTRACT

The present invention relates to compositions and methods for the prevention or the treatment of lung cancer, wherein the compositions comprise an antibody binding to progastrin and the methods comprise the use of an antibody binding to progastrin.

18 Claims, 1 Drawing Sheet
Specification includes a Sequence Listing.

(56) References Cited

FOREIGN PATENT DOCUMENTS

| WO | WO 2008/076454 A1 | 6/2008 | |
|---|---|---|---|
| WO | WO-2011045080 A2 * | 4/2011 | ............... A61P 1/00 |
| WO | WO 2011/083090 A2 | 7/2011 | |
| WO | WO 2012/013609 A1 | 2/2012 | |
| WO | WO-2016066671 A1 * | 5/2016 | .............. A61P 35/00 |

OTHER PUBLICATIONS

Cho, *Potentially useful biomarkers for the diagnosis, treatment and prognosis of lung cancer*, 61 Biomedicine & Pharmacotherapy 515-519 (Oct. 2007).

Hardavella et al., *Lung cancer stem cells-characteristics, phenotype*, 5(3) Translational Lung Cancer Research 272-279 (2016).

Hinman et al., *Preparation and Characterization of Monoclonal Antibody Conjugates of the Calicheamicins: A Novel and Potent Family of Antitumor Antibiotics*, 53(14) Cancer Research 3336-3342 (Jul. 15, 1993).

Jones et al., *Replacing the complementarity-determining regions in a human antibody with those from a mouse*, 321 Nature 522-525 (May 29, 1986).

Kaas et al., *IMGT/3Dstructure-DB and IMGT/StructuralQuery, a database and a tool for immunoglobulin, T cell receptor and MHC structural data*, 32 Nucleic Acids Research D208-D210 (Jan. 2004).

Kaas et al., *IMGT Colliers de Perles: Standardized Sequence-Structure Representations of the IgSF and MhcSF Superfamily Domains*, 2(1) Current Bioinformatics 21-30 (Jan. 2007).

Koh et al., *Glycine-Extended Gastrin Promotes the Growth of Lung Cancer*, 64 Cancer Research 196-201 (Jan. 1, 2004).

Korpanty et al., *Update on anti-angiogenic therapy in non-small cell lung cancer: Are we making progress?*, 3(1) Journal of Thoracic Disease 19-29 (Mar. 2011).

LeFranc, *Unique database numbering system for immunogenetic analysis*, 18(11) Immunology Today 509 (Nov. 1997).

LeFranc, *The IMGT Unique Numbering for Immunoglobulins, T-Cell Receptors, and Ig-Like Domains*, 7(4) The Immunologist 132-136 (1999).

LeFranc et al., *IMGT unique numbering for immunoglobulin and T cell receptor variable domains and Ig superfamily V-like domains*, 27(1) Developmental and Comparative Immunology 55-77 (Jan. 2003).

Leja et al., *Implementation of Gastric Cancer Screening—The Global Experience*, 28(6) BestPract Res Clin Gastroenterol 1093-1106 (Dec. 2014).

Liu et al., *Eradication of large colon tumor xenografts by targeted delivery of maytansinoids*, 93(16) PNAS USA 8618-8623 (Aug. 1996).

Lode et al., *Targeted Therapy with a Novel Enediyene Antibiotic Calicheamicin $\Theta^1{}_1$ Effectively Suppresses Growth and Dissemination of Liver Metastases in a Syngeneic Model of Murine Neuroblastoma*, 58(14) Cancer Research 2925-2928 (Jul. 15, 1998).

Mandler et al., *Synthesis and Evaluation of Antiproliferative Activity of a Geldanamycin-Herceptin™ Immunoconjugate*, 10 Bioorganic & Medicinal Chemistry Letters 1025-1028 (2000).

Mandler et al., *Immunoconjugates of Geldanamycin and Anti-HER2 Monoclonal Antibodies: Antiproliferative Activity on Human Breast Carcinoma Cell Lines*, 92(19) Journal of the National Cancer Institute 1573-1581 (Oct. 4, 2000).

Padlan, *A Possible Procedure for Reducing the Immunogenicity of Antibody Variable Domains While Preserving Their Ligand-Binding Properties*, 28(4/5) Molecular Immunology 489-498 (1991).

Payne, *Progress in immunoconjugate cancer therapeutics*, 3(3) Cancer Cell 207-212 (Mar. 2003).

Pepe et al., *Pivotal Evaluation of the Accuracy of a Biomarker Used for Classification or Prediction: Standards for Study Design*, 100(20) Journal of National Cancer Institute 1432-1438 (Oct. 15, 2008).

Roguska et al., *Humanization of murine monoclonal antibodies through variable domain resurfacing*, 91(3) Proc. Natl. Acad. Sci. USA 969-973 (Feb. 1994).

Ruiz et al., *IMGT Gene Identification and Colliers de Perles of Human Immunoglobulins with known 3D Structures*, 53 (10/11) Immunogenetics 857-883 (Feb. 2002).

Singer et al., *Optimal Humanization of 1B4, an Anti-CD18 Murine Monoclonal Antibody, Is Achieved by Correct Choice of Human V-Region Framework Sequences*, 150(7) The Journal of Immunology 2844-2857 (Apr. 1, 1993).

Studnicka et al., *Human-engineered monoclonal antibodies retain full specific binding activity by preserving non-CDR complementarity-modulating residues*, 7(6) Protein Engineering 805-814 (1994).

Vitetta et al., *Redesigning Nature's Poisons to Create Anti-Tumor Reagents*, 238 Science 1098-1104 (Nov. 20, 1987).

Yanaoka et al., *Cancer High-Risk Subjects Identified by Serum Pepsinogen Tests: Outcomes after 10-Year Follow-up in Asymptomatic Middle-Aged Males*, 17(4) Cancer Epidemiol Biomarkers Prev 838-845 (Apr. 2008).

International Search Report (Form PCT/ISA/210) dated May 24, 2018, by the European Patent Office in corresponding International Application No. PCT/EP2018/058346 (3 pages).

\* cited by examiner

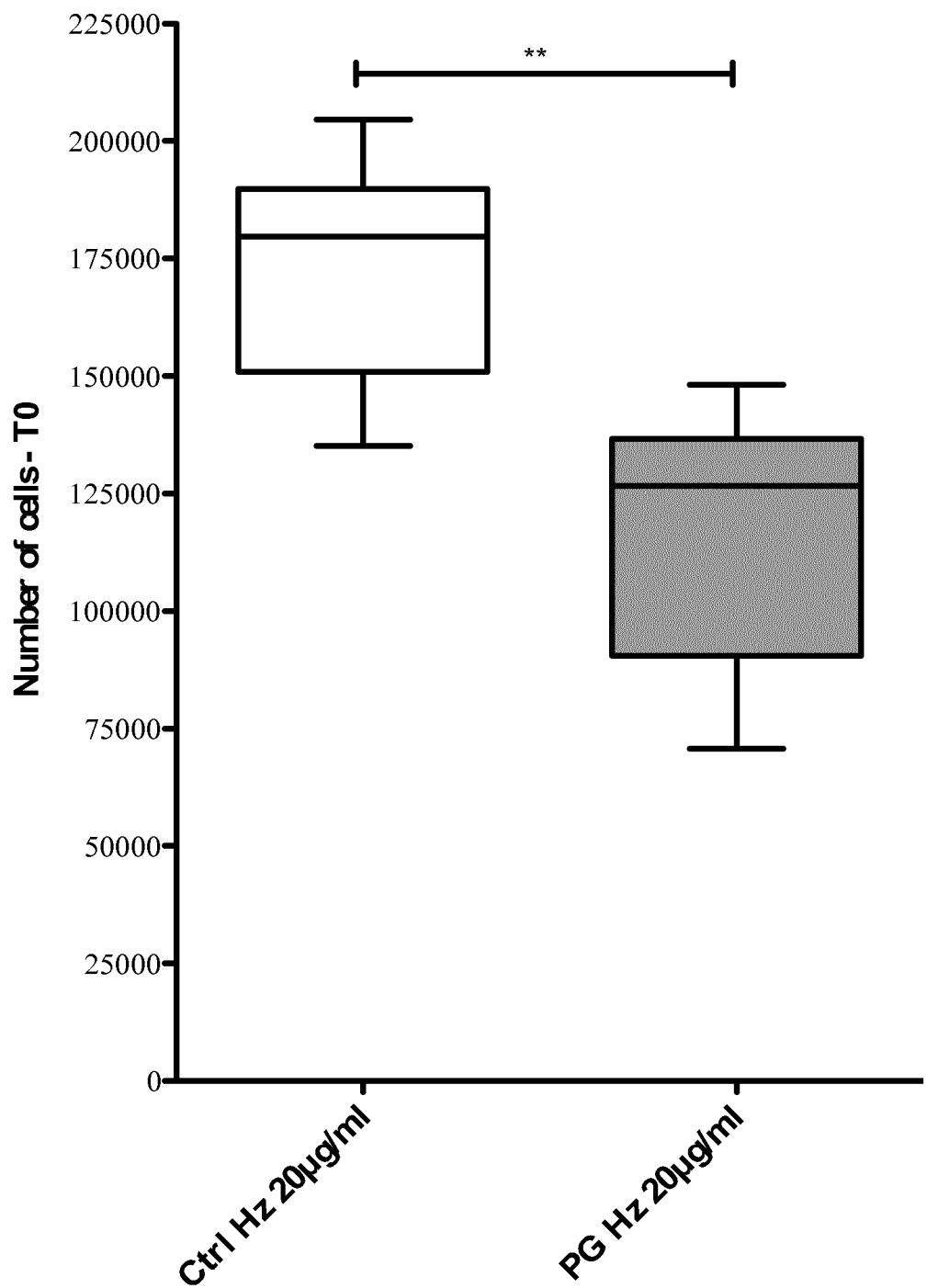

SEQUENCE LISTING

```
<160> NUMBER OF SEQ ID NOS: 78

<210> SEQ ID NO 1
<211> LENGTH: 80
<212> TYPE: PRT
<213> ORGANISM: Homo sapiens

<400> SEQUENCE: 1

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 2
<211> LENGTH: 14
<212> TYPE: PRT
<213> ORGANISM: Artificial
<220> FEATURE:
<223> OTHER INFORMATION: Amino acids 1-14 N-terminal extremity of human
      progastrin

<400> SEQUENCE: 2

Ser Trp Lys Pro Arg Ser Gln Gln Pro Asp Ala Pro Leu Gly
1               5                   10

<210> SEQ ID NO 3
<211> LENGTH: 26
<212> TYPE: PRT
<213> ORGANISM: Artificial
<220> FEATURE:
<223> OTHER INFORMATION: Amino acids 55-80 C-terminal extremity of human
      progastrin

<400> SEQUENCE: 3

Gln Gly Pro Trp Leu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 4
<211> LENGTH: 8
<212> TYPE: PRT
<213> ORGANISM: Artificial
<220> FEATURE:
<223> OTHER INFORMATION: synthetic peptide

<400> SEQUENCE: 4

Gly Tyr Ile Phe Thr Ser Tyr Trp
```

```
1               5

<210> SEQ ID NO 5
<211> LENGTH: 8
<212> TYPE: PRT
<213> ORGANISM: Artificial
<220> FEATURE:
<223> OTHER INFORMATION: synthetic peptide

<400> SEQUENCE: 5

Phe Tyr Pro Gly Asn Ser Asp Ser
1               5

<210> SEQ ID NO 6
<211> LENGTH: 8
<212> TYPE: PRT
<213> ORGANISM: Artificial
<220> FEATURE:
<223> OTHER INFORMATION: synthetic peptide

<400> SEQUENCE: 6

Thr Arg Arg Asp Ser Pro Gln Tyr
1               5

<210> SEQ ID NO 7
<211> LENGTH: 11
<212> TYPE: PRT
<213> ORGANISM: Artificial
<220> FEATURE:
<223> OTHER INFORMATION: synthetic peptide

<400> SEQUENCE: 7

Gln Ser Ile Val His Ser Asn Gly Asn Thr Tyr
1               5                   10

<210> SEQ ID NO 8
<211> LENGTH: 3
<212> TYPE: PRT
<213> ORGANISM: Artificial
<220> FEATURE:
<223> OTHER INFORMATION: synthetic peptide

<400> SEQUENCE: 8

Lys Val Ser
1

<210> SEQ ID NO 9
<211> LENGTH: 9
<212> TYPE: PRT
<213> ORGANISM: Artificial
<220> FEATURE:
<223> OTHER INFORMATION: synthetic peptide

<400> SEQUENCE: 9

Phe Gln Gly Ser His Val Pro Phe Thr
1               5

<210> SEQ ID NO 10
<211> LENGTH: 7
<212> TYPE: PRT
<213> ORGANISM: Artificial
<220> FEATURE:
<223> OTHER INFORMATION: synthetic peptide

<400> SEQUENCE: 10

Gly Tyr Thr Phe Ser Ser Trp
1               5
```

```
<210> SEQ ID NO 11
<211> LENGTH: 8
<212> TYPE: PRT
<213> ORGANISM: Artificial
<220> FEATURE:
<223> OTHER INFORMATION: synthetic peptide

<400> SEQUENCE: 11

Phe Leu Pro Gly Ser Gly Ser Thr
1               5

<210> SEQ ID NO 12
<211> LENGTH: 11
<212> TYPE: PRT
<213> ORGANISM: Artificial
<220> FEATURE:
<223> OTHER INFORMATION: synthetic peptide

<400> SEQUENCE: 12

Ala Thr Asp Gly Asn Tyr Asp Trp Phe Ala Tyr
1               5                   10

<210> SEQ ID NO 13
<211> LENGTH: 11
<212> TYPE: PRT
<213> ORGANISM: Artificial
<220> FEATURE:
<223> OTHER INFORMATION: synthetic peptide

<400> SEQUENCE: 13

Gln Ser Leu Val His Ser Ser Gly Val Thr Tyr
1               5                   10

<210> SEQ ID NO 14
<211> LENGTH: 3
<212> TYPE: PRT
<213> ORGANISM: Artificial
<220> FEATURE:
<223> OTHER INFORMATION: synthetic peptide

<400> SEQUENCE: 14

Lys Val Ser
1

<210> SEQ ID NO 15
<211> LENGTH: 9
<212> TYPE: PRT
<213> ORGANISM: Artificial
<220> FEATURE:
<223> OTHER INFORMATION: synthetic peptide

<400> SEQUENCE: 15

Ser Gln Ser Thr His Val Pro Pro Thr
1               5

<210> SEQ ID NO 16
<211> LENGTH: 8
<212> TYPE: PRT
<213> ORGANISM: Artificial
<220> FEATURE:
<223> OTHER INFORMATION: synthetic peptide

<400> SEQUENCE: 16

Gly Tyr Thr Phe Thr Ser Tyr Tyr
1               5
```

<210> SEQ ID NO 17
<211> LENGTH: 8
<212> TYPE: PRT
<213> ORGANISM: Artificial
<220> FEATURE:
<223> OTHER INFORMATION: synthetic peptide

<400> SEQUENCE: 17

Ile Asn Pro Ser Asn Gly Gly Thr
1               5

<210> SEQ ID NO 18
<211> LENGTH: 10
<212> TYPE: PRT
<213> ORGANISM: Artificial
<220> FEATURE:
<223> OTHER INFORMATION: synthetic peptide

<400> SEQUENCE: 18

Thr Arg Gly Gly Tyr Tyr Pro Phe Asp Tyr
1               5                   10

<210> SEQ ID NO 19
<211> LENGTH: 11
<212> TYPE: PRT
<213> ORGANISM: Artificial
<220> FEATURE:
<223> OTHER INFORMATION: synthetic peptide

<400> SEQUENCE: 19

Gln Ser Leu Leu Asp Ser Asp Gly Lys Thr Tyr
1               5                   10

<210> SEQ ID NO 20
<211> LENGTH: 3
<212> TYPE: PRT
<213> ORGANISM: Artificial
<220> FEATURE:
<223> OTHER INFORMATION: synthetic peptide

<400> SEQUENCE: 20

Leu Val Ser
1

<210> SEQ ID NO 21
<211> LENGTH: 9
<212> TYPE: PRT
<213> ORGANISM: Artificial
<220> FEATURE:
<223> OTHER INFORMATION: synthetic peptide

<400> SEQUENCE: 21

Trp Gln Gly Thr His Ser Pro Tyr Thr
1               5

<210> SEQ ID NO 22
<211> LENGTH: 9
<212> TYPE: PRT
<213> ORGANISM: Artificial
<220> FEATURE:
<223> OTHER INFORMATION: synthetic peptide

<400> SEQUENCE: 22

Gly Tyr Ser Ile Thr Ser Asp Tyr Ala
1               5

```
<210> SEQ ID NO 23
<211> LENGTH: 7
<212> TYPE: PRT
<213> ORGANISM: Artificial
<220> FEATURE:
<223> OTHER INFORMATION: synthetic peptide

<400> SEQUENCE: 23

Ile Ser Phe Ser Gly Tyr Thr
1               5

<210> SEQ ID NO 24
<211> LENGTH: 14
<212> TYPE: PRT
<213> ORGANISM: Artificial
<220> FEATURE:
<223> OTHER INFORMATION: synthetic peptide

<400> SEQUENCE: 24

Ala Arg Glu Val Asn Tyr Gly Asp Ser Tyr His Phe Asp Tyr
1               5                   10

<210> SEQ ID NO 25
<211> LENGTH: 7
<212> TYPE: PRT
<213> ORGANISM: Artificial
<220> FEATURE:
<223> OTHER INFORMATION: synthetic peptide

<400> SEQUENCE: 25

Ser Gln His Arg Thr Tyr Thr
1               5

<210> SEQ ID NO 26
<211> LENGTH: 7
<212> TYPE: PRT
<213> ORGANISM: Artificial
<220> FEATURE:
<223> OTHER INFORMATION: synthetic peptide

<400> SEQUENCE: 26

Val Lys Lys Asp Gly Ser His
1               5

<210> SEQ ID NO 27
<211> LENGTH: 13
<212> TYPE: PRT
<213> ORGANISM: Artificial
<220> FEATURE:
<223> OTHER INFORMATION: synthetic peptide

<400> SEQUENCE: 27

Gly Val Gly Asp Ala Ile Lys Gly Gln Ser Val Phe Val
1               5                   10

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

Gly Phe Thr Phe Thr Thr Tyr Ala
1               5

<210> SEQ ID NO 29
```

```
<211> LENGTH: 8
<212> TYPE: PRT
<213> ORGANISM: Artificial
<220> FEATURE:
<223> OTHER INFORMATION: synthetic peptide

<400> SEQUENCE: 29

Ile Ser Ser Gly Gly Thr Tyr Thr
1               5

<210> SEQ ID NO 30
<211> LENGTH: 10
<212> TYPE: PRT
<213> ORGANISM: Artificial
<220> FEATURE:
<223> OTHER INFORMATION: synthetic peptide

<400> SEQUENCE: 30

Ala Thr Gln Gly Asn Tyr Ser Leu Asp Phe
1               5                   10

<210> SEQ ID NO 31
<211> LENGTH: 11
<212> TYPE: PRT
<213> ORGANISM: Artificial
<220> FEATURE:
<223> OTHER INFORMATION: synthetic peptide

<400> SEQUENCE: 31

Lys Ser Leu Arg His Thr Lys Gly Ile Thr Phe
1               5                   10

<210> SEQ ID NO 32
<211> LENGTH: 3
<212> TYPE: PRT
<213> ORGANISM: Artificial
<220> FEATURE:
<223> OTHER INFORMATION: synthetic peptide

<400> SEQUENCE: 32

Gln Met Ser
1

<210> SEQ ID NO 33
<211> LENGTH: 9
<212> TYPE: PRT
<213> ORGANISM: Artificial
<220> FEATURE:
<223> OTHER INFORMATION: synthetic peptide

<400> SEQUENCE: 33

Ala Gln Asn Leu Glu Leu Pro Leu Thr
1               5

<210> SEQ ID NO 34
<211> LENGTH: 8
<212> TYPE: PRT
<213> ORGANISM: Artificial
<220> FEATURE:
<223> OTHER INFORMATION: synthetic peptide

<400> SEQUENCE: 34

Gly Phe Ile Phe Ser Ser Tyr Gly
1               5

<210> SEQ ID NO 35
<211> LENGTH: 8
```

```
<212> TYPE: PRT
<213> ORGANISM: Artificial
<220> FEATURE:
<223> OTHER INFORMATION: synthetic peptide

<400> SEQUENCE: 35

Ile Asn Thr Phe Gly Asp Arg Thr
1               5

<210> SEQ ID NO 36
<211> LENGTH: 7
<212> TYPE: PRT
<213> ORGANISM: Artificial
<220> FEATURE:
<223> OTHER INFORMATION: synthetic peptide

<400> SEQUENCE: 36

Ala Arg Gly Thr Gly Thr Tyr
1               5

<210> SEQ ID NO 37
<211> LENGTH: 11
<212> TYPE: PRT
<213> ORGANISM: Artificial
<220> FEATURE:
<223> OTHER INFORMATION: synthetic peptide

<400> SEQUENCE: 37

Gln Ser Leu Leu Asp Ser Asp Gly Lys Thr Tyr
1               5                   10

<210> SEQ ID NO 38
<211> LENGTH: 3
<212> TYPE: PRT
<213> ORGANISM: Artificial
<220> FEATURE:
<223> OTHER INFORMATION: synthetic peptide

<400> SEQUENCE: 38

Leu Val Ser
1

<210> SEQ ID NO 39
<211> LENGTH: 9
<212> TYPE: PRT
<213> ORGANISM: Artificial
<220> FEATURE:
<223> OTHER INFORMATION: synthetic peptide

<400> SEQUENCE: 39

Trp Gln Gly Thr His Phe Pro Gln Thr
1               5

<210> SEQ ID NO 40
<211> LENGTH: 10
<212> TYPE: PRT
<213> ORGANISM: Artificial
<220> FEATURE:
<223> OTHER INFORMATION: Amino acids 71-80 C-terminal extremity of human
      progastrin

<400> SEQUENCE: 40

Phe Gly Arg Arg Ser Ala Glu Asp Glu Asn
1               5                   10

<210> SEQ ID NO 41
<211> LENGTH: 115
```

```
<212> TYPE: PRT
<213> ORGANISM: Artificial
<220> FEATURE:
<223> OTHER INFORMATION: synthetic peptide

<400> SEQUENCE: 41

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115

<210> SEQ ID NO 42
<211> LENGTH: 112
<212> TYPE: PRT
<213> ORGANISM: Artificial
<220> FEATURE:
<223> OTHER INFORMATION: synthetic peptide

<400> SEQUENCE: 42

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110

<210> SEQ ID NO 43
<211> LENGTH: 118
<212> TYPE: PRT
<213> ORGANISM: Artificial
<220> FEATURE:
<223> OTHER INFORMATION: synthetic peptide

<400> SEQUENCE: 43

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Ser
            20                  25                  30

Trp Ile Glu Trp Leu Lys Gln Arg Pro Gly His Gly Leu Glu Trp Ile
```

```
                    35                  40                  45

Gly Glu Phe Leu Pro Gly Ser Gly Ser Thr Asp Tyr Asn Glu Lys Phe
    50                  55                  60

Lys Gly Lys Ala Thr Phe Thr Ala Asp Thr Ser Ser Asp Thr Ala Tyr
65                  70                  75                  80

Met Leu Leu Ser Ser Leu Thr Ser Glu Asp Ser Ala Val Tyr Tyr Cys
                85                  90                  95

Ala Thr Asp Gly Asn Tyr Asp Trp Phe Ala Tyr Trp Gly Gln Gly Thr
                100                 105                 110

Leu Val Thr Val Ser Ala
            115

<210> SEQ ID NO 44
<211> LENGTH: 112
<212> TYPE: PRT
<213> ORGANISM: Artificial
<220> FEATURE:
<223> OTHER INFORMATION: synthetic peptide

<400> SEQUENCE: 44

Asp Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Ser Gly Val Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ser Gly Thr Lys Leu Glu Ile Lys
                100                 105                 110

<210> SEQ ID NO 45
<211> LENGTH: 117
<212> TYPE: PRT
<213> ORGANISM: Artificial
<220> FEATURE:
<223> OTHER INFORMATION: synthetic peptide

<400> SEQUENCE: 45

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Met Tyr Trp Val Lys Gln Arg Pro Gly Gln Gly Leu Glu Trp Ile
            35                  40                  45

Gly Glu Ile Asn Pro Ser Asn Gly Gly Thr Asn Phe Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Gly Tyr Tyr Pro Phe Asp Tyr Trp Gly Gln Gly Thr Thr
                100                 105                 110
```

Leu Thr Val Ser Ser
        115

<210> SEQ ID NO 46
<211> LENGTH: 112
<212> TYPE: PRT
<213> ORGANISM: Artificial
<220> FEATURE:
<223> OTHER INFORMATION: synthetic peptide

<400> SEQUENCE: 46

Asp Val Val Met Thr Gln Thr Pro Leu Thr Leu Ser Val Thr Ile Gly
1               5                   10                  15

Arg Pro Ala Ser Ile Ser Cys Lys Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110

<210> SEQ ID NO 47
<211> LENGTH: 121
<212> TYPE: PRT
<213> ORGANISM: Artificial
<220> FEATURE:
<223> OTHER INFORMATION: synthetic peptide

<400> SEQUENCE: 47

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Phe Ser Gly Tyr Thr Ser Tyr Asn Pro Ser Leu
    50                  55                  60

Lys Ser Arg Ile Ser Val Thr Arg Asp Thr Ser Arg Asn Gln Phe Phe
65                  70                  75                  80

Leu Gln Leu Thr Ser Val Thr Thr Glu Asp Thr Ala Thr Tyr Tyr Cys
                85                  90                  95

Ala Arg Glu Val Asn Tyr Gly Asp Ser Tyr His Phe Asp Tyr Trp Gly
            100                 105                 110

Gln Gly Thr Ile Val Thr Val Ser Ser
        115                 120

<210> SEQ ID NO 48
<211> LENGTH: 115
<212> TYPE: PRT
<213> ORGANISM: Artificial
<220> FEATURE:
<223> OTHER INFORMATION: synthetic peptide

<400> SEQUENCE: 48

Gln Leu Ala Leu Thr Gln Ser Ser Ser Ala Ser Phe Ser Leu Gly Ala

```
                1               5                  10                 15
        Ser Ala Lys Leu Thr Cys Thr Leu Ser Ser Gln His Arg Thr Tyr Thr
                        20                  25                 30

Ile Glu Trp Tyr Gln Gln Ser Leu Lys Pro Pro Lys Tyr Val Met
                        35                  40                 45

Glu Val Lys Lys Asp Gly Ser His Ser Thr Gly His Gly Ile Pro Asp
            50                  55                 60

Arg Phe Ser Gly Ser Ser Gly Ala Asp Arg Tyr Leu Ser Ile Ser
        65                  70                  75                 80

Asn Ile Gln Pro Glu Asp Glu Ala Ile Tyr Ile Cys Gly Val Gly Asp
                        85                  90                 95

Ala Ile Lys Gly Gln Ser Val Phe Val Phe Gly Gly Thr Lys Val
                        100                 105                110

Thr Val Leu
                115

<210> SEQ ID NO 49
<211> LENGTH: 117
<212> TYPE: PRT
<213> ORGANISM: Artificial
<220> FEATURE:
<223> OTHER INFORMATION: synthetic peptide

<400> SEQUENCE: 49

Glu Val Gln Leu Val Glu Ser Gly Gly Gly Leu Val Lys Pro Gly Gly
        1               5                  10                 15

Ser Leu Arg Leu Ser Cys Ala Ala Ser Gly Phe Thr Phe Thr Thr Tyr
                        20                  25                 30

Ala Met Ser Trp Val Arg Gln Ala Pro Gly Lys Gly Leu Glu Trp Val
                        35                  40                 45

Ala Thr Ile Ser Ser Gly Gly Thr Tyr Thr Tyr Tyr Ala Asp Ser Val
            50                  55                 60

Lys Gly Arg Phe Thr Ile Ser Arg Asp Asn Ala Lys Asn Ser Leu Tyr
        65                  70                  75                 80

Leu Gln Met Asn Ser Leu Arg Ala Glu Asp Thr Ala Val Tyr Tyr Cys
                        85                  90                 95

Ala Thr Gln Gly Asn Tyr Ser Leu Asp Phe Trp Gly Gln Gly Thr Thr
                        100                 105                110

Val Thr Val Ser Ser
                115

<210> SEQ ID NO 50
<211> LENGTH: 112
<212> TYPE: PRT
<213> ORGANISM: Artificial
<220> FEATURE:
<223> OTHER INFORMATION: synthetic peptide

<400> SEQUENCE: 50

Asp Ile Val Met Thr Gln Ser Pro Leu Ser Leu Pro Val Thr Pro Gly
        1               5                  10                 15

Glu Pro Ala Ser Ile Ser Cys Arg Ser Ser Lys Ser Leu Arg His Thr
                        20                  25                 30

Lys Gly Ile Thr Phe Leu Tyr Trp Tyr Leu Gln Lys Pro Gly Gln Ser
                        35                  40                 45

Pro Gln Leu Leu Ile Tyr Gln Met Ser Asn Leu Ala Ser Gly Val Pro
            50                  55                 60
```

```
Asp Arg Phe Ser Ser Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Leu Thr Phe Gly Gly Gly Thr Lys Val Glu Ile Lys
            100                 105                 110
```

<210> SEQ ID NO 51
<211> LENGTH: 114
<212> TYPE: PRT
<213> ORGANISM: Artificial
<220> FEATURE:
<223> OTHER INFORMATION: synthetic peptide

<400> SEQUENCE: 51

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Ile Phe Ser Ser Tyr
             20                  25                  30

Gly Met Ser Trp Val Arg Gln Ser Pro Asp Arg Arg Leu Glu Leu Val
         35                  40                  45

Ala Ser Ile Asn Thr Phe Gly Asp Arg Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Thr Ser Leu Lys Ser Glu Asp Thr Ala Ile Tyr Tyr Cys
                 85                  90                  95

Ala Arg Gly Thr Gly Thr Tyr Trp Gly Gln Gly Thr Thr Leu Thr Val
            100                 105                 110

Ser Ser
```

<210> SEQ ID NO 52
<211> LENGTH: 112
<212> TYPE: PRT
<213> ORGANISM: Artificial
<220> FEATURE:
<223> OTHER INFORMATION: synthetic peptide

<400> SEQUENCE: 52

```
Asp Val Val Leu Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Gln Thr Phe Gly Gly Gly Thr Lys Leu Glu Ile Lys
            100                 105                 110
```

<210> SEQ ID NO 53
<211> LENGTH: 115
<212> TYPE: PRT
<213> ORGANISM: Artificial
<220> FEATURE:

<223> OTHER INFORMATION: synthetic peptide

<400> SEQUENCE: 53

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Thr Ser Tyr
            20                  25                  30
Trp Val His Trp Val Arg Gln Ala Pro Gly Gln Arg Leu Glu Trp Met
        35                  40                  45
Gly Gly Phe Tyr Pro Gly Asn Ser Asp Ser Arg Tyr Ser Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Arg Asp Ser Pro Gln Tyr Trp Gly Gln Gly Thr Leu Val Thr
            100                 105                 110
Val Ser Ser
        115
```

<210> SEQ ID NO 54
<211> LENGTH: 112
<212> TYPE: PRT
<213> ORGANISM: Artificial
<220> FEATURE:
<223> OTHER INFORMATION: synthetic peptide

<400> SEQUENCE: 54

```
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Ile Val His Ser
            20                  25                  30
Asn Gly Asn Thr Tyr Leu Glu Trp Phe Gln Gln Arg Pro Gly Gln Ser
        35                  40                  45
Pro Arg Arg Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Phe Thr Phe Gly Gly Gly Thr Lys Val Glu Ile Lys
            100                 105                 110
```

<210> SEQ ID NO 55
<211> LENGTH: 118
<212> TYPE: PRT
<213> ORGANISM: Artificial
<220> FEATURE:
<223> OTHER INFORMATION: synthetic peptide

<400> SEQUENCE: 55

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ser Ser Ser
            20                  25                  30
Trp Met His Trp Val Arg Gln Ala Pro Gly Gln Gly Leu Glu Trp Met
        35                  40                  45
Gly Ile Phe Leu Pro Gly Ser Gly Ser Thr Asp Tyr Ala Gln Lys Phe
```

```
                    50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Ala Thr Asp Gly Asn Tyr Asp Trp Phe Ala Tyr Trp Gly Gln Gly Thr
                    100                 105                 110

Leu Val Thr Val Ser Ser
                115
```

<210> SEQ ID NO 56
<211> LENGTH: 112
<212> TYPE: PRT
<213> ORGANISM: Artificial
<220> FEATURE:
<223> OTHER INFORMATION: synthetic peptide

<400> SEQUENCE: 56

```
Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Val His Ser
                 20                  25                  30

Ser Gly Val Thr Tyr Leu Tyr Trp Tyr Leu Gln Lys Pro Gly Gln Ser
             35                  40                  45

Pro Gln Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Pro Thr Phe Gly Gln Gly Thr Lys Leu Glu Ile Lys
                100                 105                 110
```

<210> SEQ ID NO 57
<211> LENGTH: 117
<212> TYPE: PRT
<213> ORGANISM: Artificial
<220> FEATURE:
<223> OTHER INFORMATION: synthetic peptide

<400> SEQUENCE: 57

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met Tyr Trp Val Arg Gln Ala Pro Gly Gln Gly Leu Glu Trp Met
             35                  40                  45

Gly Ile Ile Asn Pro Ser Asn Gly Gly Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Gly Gly Tyr Tyr Pro Phe Asp Tyr Trp Gly Gln Gly Thr Thr
                100                 105                 110

Val Thr Val Ser Ser
            115
```

<210> SEQ ID NO 58
<211> LENGTH: 117
<212> TYPE: PRT
<213> ORGANISM: Artificial
<220> FEATURE:
<223> OTHER INFORMATION: synthetic peptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Asn Gly Gly Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 59
<211> LENGTH: 117
<212> TYPE: PRT
<213> ORGANISM: Artificial
<220> FEATURE:
<223> OTHER INFORMATION: synthetic peptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Met
            35                  40                  45

Gly Glu Ile Asn Pro Ser Asn Gly Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 60
<211> LENGTH: 112
<212> TYPE: PRT
<213> ORGANISM: Artificial
<220> FEATURE:
<223> OTHER INFORMATION: synthetic peptide

<400> SEQUENCE: 60

Asp Val Val Met Thr Gln Ser Pro Leu Ser Leu Pro Val Thr Leu Gly

```
1               5                   10                  15
Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Asn Arg Asp Ser Gly Val Pro
            50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Trp Gln Gly
                    85                  90                  95

Thr His Ser Pro Tyr Thr Phe Gly Gln Gly Thr Lys Leu Glu Ile Lys
                100                 105                 110

<210> SEQ ID NO 61
<211> LENGTH: 112
<212> TYPE: PRT
<213> ORGANISM: Artificial
<220> FEATURE:
<223> OTHER INFORMATION: synthetic peptide

<400> SEQUENCE: 61

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
            50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Trp Gln Gly
                    85                  90                  95

Thr His Ser Pro Tyr Thr Phe Gly Gln Gly Thr Lys Leu Glu Ile Lys
                100                 105                 110

<210> SEQ ID NO 62
<211> LENGTH: 112
<212> TYPE: PRT
<213> ORGANISM: Artificial
<220> FEATURE:
<223> OTHER INFORMATION: synthetic peptide

<400> SEQUENCE: 62

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Glu Arg Asp Ser Gly Val Pro
            50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Trp Gln Gly
                    85                  90                  95
```

Thr His Ser Pro Tyr Thr Phe Gly Gln Gly Thr Lys Leu Glu Ile Lys
            100                 105                 110

<210> SEQ ID NO 63
<211> LENGTH: 121
<212> TYPE: PRT
<213> ORGANISM: Artificial
<220> FEATURE:
<223> OTHER INFORMATION: synthetic peptide

<400> SEQUENCE: 63

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120

<210> SEQ ID NO 64
<211> LENGTH: 121
<212> TYPE: PRT
<213> ORGANISM: Artificial
<220> FEATURE:
<223> OTHER INFORMATION: synthetic peptide

<400> SEQUENCE: 64

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120

<210> SEQ ID NO 65
<211> LENGTH: 121
<212> TYPE: PRT
<213> ORGANISM: Artificial
<220> FEATURE:
<223> OTHER INFORMATION: synthetic peptide

```
<400> SEQUENCE: 65

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 66
<211> LENGTH: 115
<212> TYPE: PRT
<213> ORGANISM: Artificial
<220> FEATURE:
<223> OTHER INFORMATION: synthetic peptide

<400> SEQUENCE: 66

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Thr Lys Val
            100                 105                 110

Glu Ile Lys
        115

<210> SEQ ID NO 67
<211> LENGTH: 115
<212> TYPE: PRT
<213> ORGANISM: Artificial
<220> FEATURE:
<223> OTHER INFORMATION: synthetic peptide

<400> SEQUENCE: 67

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45
```

Lys Val Lys Lys Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 68
<211> LENGTH: 115
<212> TYPE: PRT
<213> ORGANISM: Artificial
<220> FEATURE:
<223> OTHER INFORMATION: synthetic peptide

<400> SEQUENCE: 68

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20                  25                  30

Ile Glu Trp His Gln Gln Pro Glu Lys Gly Pro Arg Tyr Leu Met
        35                  40                  45

Glu Val Lys Lys Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 69
<211> LENGTH: 117
<212> TYPE: PRT
<213> ORGANISM: Artificial
<220> FEATURE:
<223> OTHER INFORMATION: synthetic peptide

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
                20                  25                  30

Ala Met Ser Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

```
<210> SEQ ID NO 70
<211> LENGTH: 112
<212> TYPE: PRT
<213> ORGANISM: Artificial
<220> FEATURE:
<223> OTHER INFORMATION: synthetic peptide

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 71
<211> LENGTH: 117
<212> TYPE: PRT
<213> ORGANISM: Artificial
<220> FEATURE:
<223> OTHER INFORMATION: synthetic peptide

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 72
<211> LENGTH: 112
<212> TYPE: PRT
<213> ORGANISM: Artificial
<220> FEATURE:
<223> OTHER INFORMATION: synthetic peptide

<400> SEQUENCE: 72
```

(Val Thr Val Ser Ser 115 — continued from previous page at top)

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110
```

<210> SEQ ID NO 73
<211> LENGTH: 447
<212> TYPE: PRT
<213> ORGANISM: Artificial
<220> FEATURE:
<223> OTHER INFORMATION: synthetic peptide

<400> SEQUENCE: 73

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 74
<211> LENGTH: 219
<212> TYPE: PRT
<213> ORGANISM: Artificial
<220> FEATURE:
<223> OTHER INFORMATION: synthetic peptide

<400> SEQUENCE: 74

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 75
<211> LENGTH: 114
<212> TYPE: PRT
<213> ORGANISM: Artificial
<220> FEATURE:
<223> OTHER INFORMATION: synthetic peptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 76
<211> LENGTH: 114
<212> TYPE: PRT
<213> ORGANISM: Artificial
<220> FEATURE:
<223> OTHER INFORMATION: synthetic peptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 77
<211> LENGTH: 112
<212> TYPE: PRT
```

```
<213> ORGANISM: Artificial
<220> FEATURE:
<223> OTHER INFORMATION: synthetic peptide

<400> SEQUENCE: 77

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 78
<211> LENGTH: 112
<212> TYPE: PRT
<213> ORGANISM: Artificial
<220> FEATURE:
<223> OTHER INFORMATION: synthetic peptide

<400> SEQUENCE: 78

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110
```

COMPOSITIONS AND METHODS FOR TREATING LUNG CANCER

CROSS-REFERENCE TO RELATED APPLICATIONS

This application is a U.S. National Stage Application pursuant to 35 U.S.C. § 371 of International Patent Application PCT/EP2018/058346, filed on Mar. 30, 2018, and published as WO 2018/178364 on Oct. 4, 2018, which claims priority to European Patent Application 17305382.8, filed on Mar. 30, 2017, the International Patent Application PCT/EP2018/058346 is incorporated herein by reference in its entirety for all purposes.

INTRODUCTION

The present invention relates to the prevention and the treatment of cancer, more particularly it relates to methods and compositions for the prevention or the treatment of lung cancer. Compositions according to the invention comprise a progastrin-binding molecule, in particularly an anti-hPG antibody, whereas methods according to the invention comprise the use of a progastrin-binding molecule, and particularly to an anti-hPG antibody.

Lung cancer remains the most lethal malignancy in the world. Despite improvements in surgical treatment, systemic therapy, and radiotherapy, the 5-year survival rate for all patients diagnosed with lung cancer remains between 15 and 20%.

Lung cancer comprises two main types of tumors, namely small cell lung cancer (SCLC) and non-small cell lung cancer (NSCLC). SCLC represents 15-18% of all lung cancers, while NSCLC make up about 80% to 85% of lung cancers. Other types of lung cancer such as adenoid cystic carcinomas, lymphomas, and sarcomas, as well as benign lung tumors such as hamartomas are rare.

Small cell and non-small cell lung cancers are treated differently. In particular, SCLC is more responsive to chemotherapy and radiation therapy than other cell types of lung cancer. However, a cure is difficult to achieve because SCLC has a greater tendency to be widely disseminated by the time of diagnosis. To date, there are no molecular biomarkers that have been translated to widespread clinical practice of lung cancer. Treatments depend on the development of the cancer, and usually include surgery, for small-localized tumors, or chemotherapy, possibly in combination with radiation therapy.

Therefore, there is still a need for new compositions and methods for the prevention or the treatment of lung cancer.

This is the object of the present invention.

BRIEF DESCRIPTION OF THE DRAWINGS

FIG. 1:
Cell proliferation assay: NCI-H358 cells were treated with either a control antibody or the anti-hPG Hz 8CV2 (PG Hz), a C-terminal anti-hPG humanized antibody.

DETAILED DESCRIPTION OF THE INVENTION

The present invention now provides an antibody binding specifically to progastrin for use in the prevention or the treatment of lung cancer. The present invention also provides a composition for use in the prevention or the treatment of lung cancer, wherein said composition comprises an antibody binding to progastrin, and methods for the prevention or the treatment of lung cancer comprising the use of a composition comprising an antibody binding to progastrin, alone or in combination with any other known prevention or therapeutic methods against lung cancer.

The anti-hPG antibodies described herein, particularly the neutralizing anti-hPG antibodies, inhibit PG-dependent proliferation of lung tumor cells, making them useful therapeutic agents for the treatment of lung cancer. Accordingly, also provided are pharmaceutical compositions comprising an anti-hPG antibody and methods of using the anti-hPG antibodies and/or pharmaceutical compositions to treat lung cancer. The pharmaceutical compositions can be formulated for any convenient route of administration, including, e.g., parenteral, subcutaneous or intravenous injection, and will typically include an anti-hPG antibody, and one or more acceptable carriers, excipients, and/or diluent suitable for the desired mode of administration, and can include other optional components as will be described further below. For therapeutic uses, the compositions can be packaged in unit dosage form for ease of use.

The treatment methods generally comprise administering to a subject in need of treatment, for example a subject diagnosed with lung cancer, an amount of an anti-PG antibody and/or pharmaceutical composition thereof effective to provide a therapeutic benefit. Therapeutic benefit, described below in more detail, includes any amelioration of lung cancer, for example, slowing or halting the progression of lung cancer, reducing the severity of lung cancer, inhibiting the growth of lung tumors or the proliferation of lung cancer cells, reducing the size of lung tumors, and/or reducing PG serum levels in lung cancer patients. The subject can be a human or non-human, including a domesticated animal (e.g., cat, dog, cow, pig, horse) or a non-domesticated animal. Preferably, the subject to be treated is a human. Subjects in whom anti-hPG antibody therapy is useful can be: patients in any stage of disease progression (e.g., lung cancer Stage 0, I, II, III, or IV), patients who have received therapy for lung cancer (e.g., chemotherapy, radiation therapy, surgical resection) or patients who are receiving other therapy for lung cancer.

Methods are also provided for inhibiting the growth of a lung cancer stem cell in a patient by administering to a patient in need of inhibition of growth of a lung cancer stem cell an anti-PG antibody and/or pharmaceutical composition thereof in an amount effective to inhibit said lung cancer stem cell.

In a number of embodiments, the anti-PG antibodies are effective to reduce the proliferation or increase the differentiation or rate of cell death of lung cancer stem cells, or reduce the blood concentration of progastrin in treated patients. In other embodiments, the anti-PG antibodies and/or pharmaceutical composition thereof can be administered concurrently with or after a second therapeutic agent effective to inhibit the growth of colorectal cancer stem cells, for example, an antibody having specificity other than for progastrin.

Treatment with anti-hPG antibodies as described herein can be combined with, or adjunctive to, other therapy. Non-limiting examples of other therapy for lung cancer include chemotherapeutic treatment, radiation therapy, surgical resection, and antibody therapy, as described herein. In a specific example, anti-hPG antibodies are administered in combination with chemotherapeutic agents. In another specific example, anti-hPG antibodies are administered adjunctive to surgical resection.

The present invention also relates to pharmaceutical compositions comprising the anti-PG antibodies, preferably with a pharmaceutically acceptable carrier and/or an excipient. In some embodiments, the pharmaceutical composition further comprises a second therapeutic agent. In some embodiment, the second therapeutic agent is a biological agent or a chemotherapeutic agent. Examples of biological agents include anti-EGFR monoclonal antibodies and anti-VEGF monoclonal antibodies, whereas chemotherapeutic agents comprise such compounds as e.g. alkylating agents, anti-metabolites, anti-tumor antibiotics, mitotic inhibitors, chromatin function inhibitors, anti-angiogenesis agents, anti-estrogens, anti-androgens and immunomodulators.

Human pre-progastrin, a 101 amino acids peptide (Amino acid sequence reference: AAB19304.1), is the primary translation product of the gastrin gene. Progastrin is formed by cleavage of the first 21 amino acids (the signal peptide) from preprogastrin. The 80 amino-acid chain of progastrin is further processed by cleavage and modifying enzymes to several biologically active gastrin hormone forms: gastrin 34 (G34) and glycine-extended gastrin 34 (G34-Gly), comprising amino acids 38-71 of progastrin, gastrin 17 (G17) and glycine-extended gastrin 17 (G17-Gly), comprising amino acids 55 to 71 of progastrin.

Anti-human progastrin (anti-hPG) monoclonal antibodies and their use for diagnosis or therapy have been described in the following documents: WO 2011/083 088 for colorectal cancer, WO 2011/083 090 for breast cancer, WO 2011/083 091 for pancreatic cancer, WO 2011/116 954 for colorectal and gastrointestinal cancer, and WO 2012/013 609 and WO 2011/083089 for liver pathologies.

The present invention will become more fully understood from the detailed description given herein and from the accompanying drawings, which are given by way of illustration only and do not limit the intended scope of the invention.

In a first aspect, the present invention relates to a progastrin-binding molecule for use in the prevention or the treatment of lung cancer. The present disclosure also provides a composition for use in the prevention or the treatment of prostate cancer, wherein said composition comprises a progastrin-binding antibody, or an antigen-binding fragment thereof.

By "progastrin-binding molecule", it is herein referred to any molecule that binds progastrin, but does not bind gastrin-17 (G17), gastrin-34 (G34), glycine-extended gastrin-17 (G17-Gly), or glycine-extended gastrin-34 (G34-Gly). The progastrin-binding molecule of the present invention may be any progastrin-binding molecule, such as, for instance, an antibody molecule or a receptor molecule. Preferably, the progastrin-binding molecule is an anti-progastrin antibody (an anti-PG antibody) or an antigen-binding fragment thereof.

The term "progastrin" designates the mammalian progastrin peptide, and particularly human progastrin. For the avoidance of doubt, without any specification, the expression "human progastrin" or "hPG" refers to the human PG of sequence SEQ ID NO:1. Human progastrin comprises notably a N-terminus and a C-terminus domains which are not present in the biologically active gastrin hormone forms mentioned above. Preferably, the sequence of said N-terminus domain is represented by SEQ ID NO:2. In another preferred embodiment, the sequence of said C-terminus domain is represented by SEQ ID NO:3.

Thus, in a first embodiment, the invention relates to an antibody which binds progastrin but not any of the other gastrin-gene derived products, for use in the treatment of lung cancer.

By "binding", "binds", or the like, it is intended that the antibody, or antigen binding fragment thereof, forms a complex with an antigen which, under physiologic conditions, is relatively stable. Methods for determining whether two molecules bind are well known in the art and include, for example, equilibrium dialysis, surface plasmon resonance, and the like. In a particular embodiment, said antibody, or antigen-binding fragment thereof, binds to progastrin with an affinity that is at least two-fold greater than its affinity for binding to a non-specific molecule such as BSA or casein. In a more particular embodiment, said antibody, or antigen-binding fragment thereof, binds only to progastrin.

The expression "lung cancer" designates a cancer that originates in tissues of the lung, usually in the cells lining air passages. A "lung cancer" as used herein encompasses in particular small cell lung cancer (SCLC), including small cell carcinoma and combined small cell carcinoma, and non-small cell lung cancers (NSCLC), including squamous cell carcinoma, large cell carcinoma, and adenocarcinoma. Other types of lung cancer such as adenoid cystic carcinomas, lymphomas, and sarcomas, as well as benign lung tumours such as hamartomas are also included in the lung cancers as used herein.

In a specific embodiment, the invention provides an anti-PG antibody for use in the prevention or the treatment of lung cancer, said antibody recognizing an epitope including an amino acid sequence corresponding to an amino acid sequence of progastrin.

In a more specific embodiment, said anti-PG antibody for use in the prevention or the treatment of lung cancer recognizes an epitope of progastrin wherein said epitope includes an amino acid sequence corresponding to an amino acid sequence of the N-terminal part of progastrin, wherein said amino acid sequence may include residues 10 to 14 of hPG, residues 9 to 14 of hPG, residues 4 to 10 of hPG, residues 2 to 10 of hPG or residues 2 to 14 of hPG, wherein the amino acid sequence of hPG is SEQ ID NO:1.

In a more specific embodiment, the anti-PG antibody for use in the prevention or the treatment of lung cancer recognizes an epitope of progastrin wherein said epitope includes an amino acid sequence corresponding to an amino acid sequence of the C-terminal part of progastrin, wherein said amino acid sequence may include residues 71 to 74 of hPG, residues 69 to 73 of hPG, residues 71 to 80 of hPG (SEQ ID NO:40), residues 76 to 80 of hPG, or residues 67 to 74 of hPG, wherein the amino acid sequence of hPG is SEQ ID NO:1.

In a more particular embodiment, the anti-PG antibody for use in the prevention or the treatment of lung cancer has an affinity for progastrin of at least 5000 nM, at least 500 nM, 100 nM, 80 nM, 60 nM, 50 nM, 40 nM, 30 nM, 20 nM, 10 nM, 7 nM, 5 nM, 4 nM, 3 nM, 2 nM, 1 nM, 0.5 nM, 0.1 nM, 50 pM, 10 pM, 5 pM, 1 pM, or at least 0.1 pM, as determined by a method such as above-described.

Preferably, the anti-PG antibody for use in preventing or treating lung cancer is a neutralizing anti-PG antibody.

The expression "neutralizing anti-PG antibody" designates an antibody that binds PG and blocks PG-dependent signalling, resulting in the inhibition of PG-induced responses in tumour cells, and particularly in lung tumour cells. Inhibiting PG-induced responses of lung cancer cells may be mediated by repression of cell differentiation, repression of cell death, and/or stimulation of cell proliferation.

The term "antibody" as used herein is intended to include polyclonal and monoclonal antibodies. An antibody (or "immunoglobulin") consists of a glycoprotein comprising at least two heavy (H) chains and two light (L) chains interconnected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Method for identifying the CDRs within light and heavy chains of an antibody and determining their sequence are well known to the skilled person. For the avoidance of doubt, in the absence of any indication in the text to the contrary, the expression CDRs means the hypervariable regions of the heavy and light chains of an antibody as defined by IMGT, wherein the IMGT unique numbering provides a standardized delimitation of the framework regions and of the complementary determining regions, CDR1-IMGT: 27 to 38, CDR2.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommie, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system. Antibodies can be of different isotypes (namely IgA, IgD, IgE, IgG or IgM).

In a particular embodiment, said progastrin-binding antibody, or an antigen-binding fragment thereof, is selected from the group consisting of: polyclonal antibodies, monoclonal antibodies, chimeric antibodies, single chain antibodies, camelized antibodies, IgA1 antibodies, IgA2 antibodies, IgD antibodies, IgE antibodies, IgG1 antibodies, IgG2 antibodies, IgG3 antibodies, IgG4 antibodies and IgM antibodies.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

The term "monoclonal antibody" designates an antibody arising from a nearly homogeneous antibody population, wherein population comprises identical antibodies except for a few possible naturally-occurring mutations which can be found in minimal proportions. A monoclonal antibody arises from the growth of a single cell clone, such as a hybridoma, and is characterized by heavy chains of one class and subclass, and light chains of one type.

By the expression "antigen-binding fragment" of an antibody, it is intended to indicate any peptide, polypeptide, or protein retaining the ability to bind to the target (also generally referred to as antigen) of the said antibody, generally the same epitope, and comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, or at least 200 contiguous amino acid residues, of the amino acid sequence of the antibody.

In a particular embodiment, the said antigen-binding fragment comprises at least one CDR of the antibody from which it is derived. Still in a preferred embodiment, the said antigen binding fragment comprises 2, 3, 4 or 5 CDRs, more preferably the 6 CDRs of the antibody from which it is derived.

The "antigen-binding fragments" can be selected, without limitation, in the group consisting of Fv, scFv (sc for single chain), Fab, F(ab')$_2$, Fab', scFv-Fc fragments or diabodies, or fusion proteins with disordered peptides such as XTEN (extended recombinant polypeptide) or PAS motifs, or any fragment of which the half-life time would be increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen-binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target.

In another particular embodiment, in a method for the diagnosis of lung cancer according to the invention, a biological sample from a subject is contacted with an antibody binding to progastrin, wherein said antibody has been obtained by an immunization method known by a person skilled in the art, wherein using as an immunogen a peptide which amino acid sequence comprises the totality or a part of the amino-acid sequence of progastrin. More particularly, said immunogen comprises a peptide chosen among:

- a peptide which amino acid sequence comprises, or consists of, the amino acid sequence of full length progastrin, and particularly full length human progastrin of SEQ ID NO:1,
- a peptide which amino acid sequence corresponds to a part of the amino acid sequence of progastrin, and particularly full length human progastrin of SEQ ID NO:1,
- a peptide which amino acid sequence corresponds to a part or to the whole amino acid sequence of the N-terminal part of progastrin, and in particular peptides comprising, or consisting of, the amino acid sequence:

```
                           (SEQ ID NO: 2)
SWKPRSQQPDAPLG,
``` and

- a peptide which amino acid sequence corresponds to a part or to the whole amino acid sequence of the C-terminal part of progastrin, and in particular peptides comprising, or consisting of, the amino acid sequence:

```
                                 (SEQ ID NO: 3)
QGPWLEEEEEAYGWMDFGRRSAEDEN,
```

- a peptide which amino acid sequence corresponds to a part of the amino acid sequence of the C-terminal part of progastrin, and in particular peptides comprising the amino acid sequence FGRRSAEDEN (SEQ ID NO:40) corresponding to amino acids 71-80 of progastrin The skilled person will realize that such immunization may be used to generate either polyclonal or monoclonal antibodies, as desired. Methods for obtaining each of these types of antibodies are well known in the art. The skilled person will thus easily select and implement a method for generating polyclonal and/or monoclonal antibodies against any given antigen.

Examples of monoclonal antibodies which were generated by using an immunogen comprising the amino-acid sequence "SWKPRSQQPDAPLG" (SEQ ID NO:2), corresponding to the amino acid sequence 1-14 of human progastrin (N-terminal extremity) include, but are not restricted to, monoclonal antibodies designated as: mAb3, mAb4, mAb16, and mAb19 and mAb20, as described in the following Table 1 to Table 4. Other monoclonal antibodies have been described, although it is not clear whether these antibodies actually bind progastrin (WO 2006/032980). Experimental results of epitope mapping show that mAb3, mAb4, mAb16, and mAb19 and mAb20 do specifically bind an epitope within said hPG N-terminal amino acid sequence. Polyclonal antibodies recognizing specifically an epitope within the N-terminus of progastrin represented by SEQ ID NO:2, have been described in the art (see e.g, WO 2011/083088).

TABLE 1

| Hybridoma deposit | mAb | Amino acid sequences | | SEQ ID NO: |
|---|---|---|---|---|
| 6B5B11C10 | mAb3 | VH CDR 1 | GYIFTSYW | SEQ ID NO: 4 |
| | | VH CDR 2 | FYPGNSDS | SEQ ID NO: 5 |
| | | VH CDR 3 | TRRDSPQY | SEQ ID NO: 6 |
| | | VL CDR 1 | QSIVHSNGNTY | SEQ ID NO: 7 |
| | | VL CDR 2 | KVS | SEQ ID NO: 8 |
| | | VL CDR 3 | FQGSHVPFT | SEQ ID NO: 9 |
| | | mVH 3 | EVQLQQSGTVLARPGASVKMSCK ASGYIFTSYWVHWVKQRPGQGLE WIGGFYPGNSDSRYNQKFKGKAT LTAVTSASTAYMDLSSLTNEDSAV YFCTRRDSPQYWGQGTTLTVSS | SEQ ID NO: 41 |
| | | mVL 3 | DVLMTQTPLSLPVSLGDQASISCR SSQSIVHSNGNTYLEWYLQKPGQS PKLLIYKVSNRFSGVPDRFSGSGS GTDFTLKISRLEAEDLGVYYCFQG SHVPFTFGGGTKLEIK | SEQ ID NO: 42 |
| | | huVH 3 | QVQLVQSGAEVKKPGASVKVSCK ASGYIFTSYWVHWVRQAPGQRLE WMGGFYPGNSDSRYSQKFQGRV TITRDTSASTAYMELSSLRSEDTAV YYCTRRDSPQYWGQGTLVTVSS | SEQ ID NO: 53 |
| | | huVL 3 | DVVMTQSPLSLPVTLGQPASISCR SSQSIVHSNGNTYLEWFQQRPGQ SPRRLIYKVSNRFSGVPDRFSGSGS GTDFTLKISRVEAEDVGVYYCFQG SHVPFTFGGGTKVEIK | SEQ ID NO: 54 |

TABLE 2

| Hybridoma deposit | mAb | Amino acid sequences | | SEQ ID NO |
|---|---|---|---|---|
| 20D2C3G2 | mAb4 | VH CDR 1 | GYTFSSW | SEQ ID NO: 10 |
| | | VH CDR 2 | FLPGSGST | SEQ ID NO: 11 |
| | | VH CDR 3 | ATDGNYDWFAY | SEQ ID NO: 12 |
| | | VL CDR 1 | QSLVHSSGVTY | SEQ ID NO: 13 |
| | | VL CDR 2 | KVS | SEQ ID NO: 14 |
| | | VL CDR 3 | SQSTHVPPT | SEQ ID NO: 15 |
| | | mVH 4 | QVQLQQSGAELMKPGASVKISCK ATGYTFSSSWIEWLKQRPGHGLE WIGEFLPGSGSTDYNEKFKGKATF TADTSSDTAYMLLSSLTSEDSAVY YCATDGNYDWFAYWGQGTLVTV SA | SEQ ID NO: 43 |
| | | mVL 4 | DLVMTQTPLSLPVSLGDQASISCR SSQSLVHSSGVTYLHWYLQKPGQ SPKLLIYKVSNRFSGVPDRFSGSGS GTDFTLKISRVEAEDLGVYFCSQS THVPPTFGSGTKLEIK | SEQ ID NO: 44 |
| | | huVH 4 | QVQLVQSGAEVKKPGASVKVSCK ASGYTFSSSWMHWVRQAPGQGL EWMGIFLPGSGSTDYAQKFQGRV TMTRDTSTSTVYMELSSLRSEDTA VYYCATDGNYDWFAYWGQGTLV TVSS | SEQ ID NO: 55 |
| | | huVL 4 | DIVMTQTPLSLSVTPGQPASISCKS SQSLVHSSGVTYLYWYLQKPGQS PQLLIYKVSNRFSGVPDRFSGSGS GTDFTLKISRVEAEDVGVYYCSQS THVPPTFGQGTKLEIK | SEQ ID NO: 56 |

TABLE 3

| Hybridoma deposit | mAb | Amino acid sequences | | SEQ ID NO |
|---|---|---|---|---|
| 1E9D9B6 | mAb16 | VH CDR 1 | GYTFTSYY | SEQ ID NO: 16 |
| | | VH CDR 2 | INPSNGGT | SEQ ID NO: 17 |
| | | VH CDR 3 | TRGGYYPFDY | SEQ ID NO: 18 |
| | | VL CDR 1 | QSLLDSDGKTY | SEQ ID NO: 19 |
| | | VL CDR 2 | LVS | SEQ ID NO: 20 |
| | | VL CDR 3 | WQGTHSPYT | SEQ ID NO: 21 |
| | | mVH 16 | QVQLQQSGAELVKPGASVKLSCK ASGYTFTSYYMYWVKQRPGQGLE WIGEINPSNGGTNFNEKFKSKATL TVDKSSSTAYMQLSSLTSEDSAVY YCTRGGYYPFDYWGQGTTLTVSS | SEQ ID NO: 45 |
| | | mVL 16 | DVVMTQTPLTLSVTIGRPASICKS SQSLLDSDGKTYLYWLLQRPGQS PKRLIYLVSELDSGVPDRITGSGSG TDFTLKISRVEAEDLGVYYCWQG THSPYTFGGGTKLEIK | SEQ ID NO: 46 |
| | | huVH 16a | QVQLVQSGAEVKKPGASVKVSCK ASGYTFTSYYMYWVRQAPGQGLE WMGIINPSNGGTSYAQKFQGRVT MTRDTSTSTVYMELSSLRSEDTAV YYCTRGGYYPFDYWGQGTTVTV SS | SEQ ID NO: 57 |
| | | huVH 16b | QVQLVQSGAEVKKPGASVKVSCK ASGYTFTSYYMHWVRQAPGQGL EWMGIINPSNGGTSYAQKFQGRV TMTRDTSTSTVYMELSSLRSEDTA VYYCTRGGYYPFDYWGQGTTVT VSS | SEQ ID NO: 58 |
| | | huVH 16c | QVQLVQSGAEVKKPGASVKVSCK ASGYTFTSYYMYWVRQAPGQGLE WMGEINPSNGGTNYAQKFQGRV TMTRDTSTSTVYMELSSLRSEDTA VYYCTRGGYYPFDYWGQGTTVT VSS | SEQ ID NO: 59 |
| | | huVL 16a | DVVMTQSPLSLPVTLGQPASISCR SSQSLLDSDGKTYLYWFQQRPGQ SPRRLIYLVSNRDSGVPDRFSGSGS GTDFTLKISRVEAEDVGVYYCWQ GTHSPYTFGQGTKLEIK | SEQ ID NO: 60 |

TABLE 3-continued

| Hybridoma deposit | mAb | Amino acid sequences | | SEQ ID NO |
|---|---|---|---|---|
| | | huVL 16b | DVVMTQSPLSLPVTLGQPASISCR SSQSLLDSDGKTYLNWFQQRPGQ SPRRLIYLVSNRDSGVPDRFSGSGS GTDFTLKISRVEAEDVGVYYCWQ GTHSPYTFGQGTKLEIK | SEQ ID NO: 61 |
| | | huVL 16c | DVVMTQSPLSLPVTLGQPASISCR SSQSLLDSDGKTYLYWFQQRPGQ SPRRLIYLVSERDSGVPDRFSGSGS GTDFTLKISRVEAEDVGVYYCWQ GTHSPYTFGQGTKLEIK | SEQ ID NO: 62 |

TABLE 4

| Hybridoma deposit | mAb | Amino acid sequences | | SEQ ID NO |
|---|---|---|---|---|
| 1B3B4F11 | mAb19 | VH CDR 1 | GYSITSDYA | SEQ ID NO: 22 |
| | | VH CDR 2 | ISFSGYT | SEQ ID NO: 23 |
| | | VH CDR 3 | AREVNYGDSYHFDY | SEQ ID NO: 24 |
| | | VL CDR 1 | SQHRTYT | SEQ ID NO: 25 |
| | | VL CDR 2 | VKKDGSH | SEQ ID NO: 26 |
| | | VL CDR 3 | GVGDAIKGQSVFV | SEQ ID NO: 27 |
| | | mVH 19 | DVQLQESGPGLVKPSQSLSLTCTV TGYSITSDYAWNWIRQFPGNKLE WMGYISFSGYTSYNPSLKSRISVTR DTSRNQFFLQLTSVTTEDTATYYC AREVNYGDSYHFDYWGQGTIVTV SS | SEQ ID NO: 47 |
| | | mVL 19 | QLALTQSSSASFSLGASAKLTCTLS SQHRTYTIEWYQQQSLKPPKYVM EVKKDGSHSTGHGIPDRFSGSSSG ADRYLSISNIQPEDEAIYICGVGDAI KGQSVFVFGGGTKVTVL | SEQ ID NO: 48 |
| | | huVH 19a | QVQLQESGPGLVKPSQTLSLTCT VSGYSITSDYAWNWIRQHPGKGL EWIGYISFSGYTYYNPSLKSRVTIS VDTSKNQFSLKLSSVTAADTAVYY CAREVNYGDSYHFDYWGQGTLV TVSS | SEQ ID NO: 63 |
| | | huVH 19b | QVQLQESGPGLVKPSQTLSLTCT VSGYSITSDYAWSWIRQHPGKGLE WIGYISFSGYTYYNPSLKSRVTISV DTSKNQFSLKLSSVTAADTAVYYC AREVNYGDSYHFDYWGQGTLVT VSS | SEQ ID NO: 64 |
| | | huVH 19c | QVQLQESGPGLVKPSQTLSLTCT VSGYSITSDYAWNWIRQHPGKGL EWIGYISFSGYTSYNPSLKSRVTIS VDTSKNQFSLKLSSVTAADTAVYY CAREVNYGDSYHFDYWGQGTLV TVSS | SEQ ID NO: 65 |
| | | huVL 19a | QLVLTQSPSASASLGASVKLTCTL SSQHRTYTIEWHQQQPEKGPRYL MKVKKDGSHSKGDGIPDRFSGSSS GAERYLTISSLQSEDEADYYCGVG DAIKGQSVFVFGGGTKVEIK | SEQ ID NO: 66 |
| | | huVL 19b | QLVLTQSPSASASLGASVKLTCTL SSQHRTYTIAWHQQQPEKGPRYL MKVKKDGSHSKGDGIPDRFSGSSS GAERYLTISSLQSEDEADYYCGVG DAIKGQSVFVFGGGTKVEIK | SEQ ID NO: 67 |
| | | huVL 19c | QLVLTQSPSASASLGASVKLTCTL SSQHRTYTIEWHQQQPEKGPRYL MEVKKDGSHSKGDGIPDRFSGSSS GAERYLTISSLQSEDEADYYCGVG DAIKGQSVFVFGGGTKVEIK | SEQ ID NO: 68 |

Examples of monoclonal antibodies that can be generated by using an immunogen comprising the amino-acid sequence "QGPWLEEEEEAYGWMDFGRRSAEDEN" (SEQ ID NO:3), (C-terminal part of progastrin) corresponding to the amino acid sequence 55-80 of human progastrin include, but are not restricted to antibodies designated as: mAb8 and mAb13 in the following Table 5 and 6. Experimental results of epitope mapping show that mAb13 do specifically bind an epitope within said hPG C-terminal amino acid sequence.

TABLE 5

| Hybridoma deposit | mAb | Amino acid sequences | | SEQ ID NO |
|---|---|---|---|---|
| 1C10D3B9 | mAb8 | VH CDR 1 | GFTFTTYA | SEQ ID NO: 28 |
| | | VH CDR 2 | ISSGGTYT | SEQ ID NO: 29 |
| | | VH CDR 3 | ATQGNYSLDF | SEQ ID NO: 30 |
| | | VL CDR 1 | KSLRHTKGITF | SEQ ID NO: 31 |
| | | VL CDR 2 | QMS | SEQ ID NO: 32 |
| | | VL CDR 3 | AQNLELPLT | SEQ ID NO: 33 |
| | | mVH 8 | EVQLVESGGGLVKPGGSLRLSCAASGFTFTTYAMSWVRQAPGKGLEWVATISSGGTYTYYADSVKGRFTISRDNAKNSLYLQMNSLRAEDTAVYYCATQGNYSLDFWGQGTTVTVSS | SEQ ID NO: 49 |
| | | mVL 8 | DIVMTQSPLSLPVTPGEPASISCRSSKSLRHTKGITFLYWYLQKPGQSPQLLIYQMSNLASGVPDRFSSSGSGTDFTLKISRVEAEDVGVYYCAQNLELPLTFGGGTKVEIK | SEQ ID NO: 50 |
| | | VH hZ8CV1 | EVQLVESGGGLVKPGGSLRLSCAASGFTFTTYAMSWVRQAPGKGLEWVSSISSGGTYTYYADSVKGRFTISRDNAKNSLYLQMNSLRAEDTAVYYCATQGNYSLDFWGQGTTVTVSS | SEQ ID NO: 69 |
| | | VL hZ8CV1 | DIVMTQSPLSLPVTPGEPASISCRSSKSLRHTKGITFLYWYLQKPGQSPQLLIYQMSNRASGVPDRFSGSGSGTDFTLKISRVEAEDVGVYYCAQNLELPLTFGGGTKVEIK | SEQ ID NO: 70 |
| | | VH hZ8CV2 | EVQLVESGGGLVKPGGSLRLSCAASGFTFTTYAMSWVRQAPGKGLEWVATISSGGTYTYYADSVKGRFTISRDNAKNSLYLQMNSLRAEDTAVYYCATQGNYSLDFWGQGTTVTVSS | SEQ ID NO: 71 |
| | | VL hZ8CV2 | DIVMTQSPLSLPVTPGEPASISCRSSKSLRHTKGITFLYWYLQKPGQSPQLLIYQMSNLASGVPDRFSSSGSGTDFTLKISRVEAEDVGVYYCAQNLELPLTFGGGTKVEIK | SEQ ID NO: 72 |
| | | CH hZ8CV2 | EVQLVESGGGLVKPGGSLRLSCAASGFTFTTYAMSWVRQAPGKGLEWVATISSGGTYTYYADSVKGRFTISRDNAKNSLYLQMNSLRAEDTAVYYCATQGNYSLDFWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | SEQ ID NO: 73 |
| | | CL hZ8CV2 | DIVMTQSPLSLPVTPGEPASISCRSSKSLRHTKGITFLYWYLQKPGQSPQLLIYQMSNLASGVPDRFSSSGSGTDFTLKISRVEAEDVGVYYCAQNLELPLTFGGGTKVEIKRTVA | SEQ ID NO: 74 |

TABLE 5-continued

| Hybridoma deposit | mAb | Amino acid sequences | SEQ ID NO |
|---|---|---|---|
| | | APSVFIFPPSDEQLKSGTASVVCL LNNFYPREAKVQWKVDNALQSG NSQESVTEQDSKDSTYSLSSTLT LSKADYEKHKVYACEVTHQGLS SPVTKSFNRGEC | |

TABLE 6

| Hybridoma deposit | mAb | Amino acid sequences | | SEQ ID NO |
|---|---|---|---|---|
| 2C6C3C7 | mAb13 | VH CDR 1 | GFIFSSYG | SEQ ID NO: 34 |
| | | VH CDR 2 | INTFGDRT | SEQ ID NO: 35 |
| | | VH CDR 3 | ARGTGTY | SEQ ID NO: 36 |
| | | VL CDR 1 | QSLLDSDGKTY | SEQ ID NO: 37 |
| | | VL CDR 2 | LVS | SEQ ID NO: 38 |
| | | VL CDR 3 | WQGTHFPQT | SEQ ID NO: 39 |
| | | mVH 13 | EVQLVESGGGLVQPGGSLKLSC AASGFIFSSYGMSWVRQSPDRRL ELVASINTFGDRTYYPDSVKGRF TISRDNAKNTLYLQMTSLKSEDT AIYYCARGTGTYWGQGTTLTVS S | SEQ ID NO: 51 |
| | | mVL 13 | DVVLTQTPLTLSVTIGQPASISCK SSQSLLDSDGKTYLNWLLQRPG QSPKRLIYLVSKLDSGVPDRFTG SGSGTDFTLKISRVEAEDLGVYY CWQGTHFPQTFGGGTKLEIK | SEQ ID NO: 52 |
| | | huVH 13a | EVQLVESGGGLVQPGGSLRLSC AASGFIFSSYGMSWVRQAPGKG LEWVANINTFGDRTYYVDSVKG RFTISRDNAKNSLYLQMNSLRAE DTAVYYCARGTGTYWGQGTLV TVSS | SEQ ID NO: 75 |
| | | huVH 13b | EVQLVESGGGLVQPGGSLRLSC AASGFIFSSYGMSWVRQAPGKG LEWVASINTFGDRTYYVDSVKG RFTISRDNAKNSLYLQMNSLRAE DTAVYYCARGTGTYWGQGTLV TVSS | SEQ ID NO: 76 |
| | | huVL 13a | DVVMTQSPLSLPVTLGQPASISC RSSQSLLDSDGKTYLNWFQQRP GQSPRRLIYLVSNRDSGVPDRFS GSGSGTDFTLKISRVEAEDVGVY YCWQGTHFPQTFGGGTKVEIK | SEQ ID NO: 77 |
| | | huVL 13b | DVVMTQSPLSLPVTLGQPASISC RSSQSLLDSDGKTYLNWFQQRP GQSPRRLIYLVSKRDSGVPDRFS GSGSGTDFTLKISRVEAEDVGVY YCWQGTHFPQTFGGGTKVEIK | SEQ ID NO: 78 |

Other examples include anti-hPG monoclonal and/or polyclonal antibodies generated by using an immunogen comprising an amino acid sequence of SEQ ID NO:40.

The terms "N-terminal anti-hPG antibodies" and "C-terminal anti-hPG antibodies" designate antibodies binding to an epitope comprising amino acids located in the N-terminal part of hPG or to an epitope comprising amino acids located in the C-terminal part of hPG, respectively. Preferably, the term "N-terminal anti-hPG antibodies" refers to antibodies binding to an epitope located in a domain of progastrin whose sequence is represented by SEQ ID NO:2. In another preferred embodiment, the term "C-terminal anti-hPG antibodies" refers to antibodies binding to an epitope located in a domain of progastrin whose sequence is represented by SEQ ID NO:3.

The term "epitope" refers to a region of an antigen that is bound by an antibody. Epitopes may be defined as structural or functional. Functional epitopes are generally a subset of the structural epitopes and have those amino acids that directly contribute to the affinity of the interaction. Epitopes may also be conformational. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. The determination of the epitope bound by an antibody may be performed by any epitope mapping technique, known by a man skilled in the art. An epitope may comprise different amino acids which located sequentially within the amino acid sequence of a protein. An epitope may also comprise amino acids which are not located sequentially within the amino acid sequence of a protein.

In a particular embodiment, said antibody is a monoclonal antibody selected in the group consisting of:

A monoclonal antibody comprising a heavy chain comprising at least one, preferentially at least two, preferentially three, of CDR-H1, CDR-H2 and CDR-H3 of amino acid sequences SEQ ID NO:4, 5 and 6, respectively, or sequences with at least 80%, preferably 85%, 90%, 95% and 98% identity after optimal alignment with sequences SEQ ID NO:4, 5 and 6, respectively, and a light chain comprising at least one, preferentially at least two, preferentially three, of CDR-L1, CDR-L2 and CDR-L3 of amino acid sequences SEQ ID NO:7, 8 and 9, respectively, or sequences with at least 80%, preferably 85%, 90%, 95% and 98% identity after optimal alignment with sequences SEQ ID NO:7, 8 and 9, respectively, A monoclonal antibody comprising a heavy chain comprising at least one, preferentially at least two, preferentially three, of CDR-H1, CDR-H2 and CDR-H3 of amino acid sequences SEQ ID NO:10, 11 and 12, respectively, or sequences with at least 80%, preferably 85%, 90%, 95% and 98% identity after optimal alignment with sequences SEQ ID NO:10, 11 and 12, respectively, and a light chain comprising at least one, preferentially at least two, preferentially three, of CDR-L1, CDR-L2 and CDR-L3 of amino acid sequences SEQ ID NO:13, 14 and 15, respectively, or sequences with at least 80%, preferably 85%, 90%, 95% and 98% identity after optimal alignment with sequences SEQ ID NO:13, 14 and 15, respectively, A monoclonal antibody comprising a heavy chain comprising at least one, preferentially at least two, preferentially three, of CDR-H1, CDR-H2 and CDR-H3 of amino acid sequences SEQ ID NO:16, 17 and 18, respectively, or sequences with at least 80%, preferably 85%, 90%, 95% and 98% identity after optimal alignment with sequences SEQ ID NO:16, 17 and 18, respectively, and a light chain comprising at least one, preferentially at least two, preferentially three, of CDR-L1, CDR-L2 and CDR-L3 of amino acid sequences SEQ ID NO:19, 20 and 21, respectively, or sequences with at least 80%, preferably 85%, 90%, 95% and 98% identity after optimal alignment with sequences SEQ ID NO:19, 20 and 21, respectively, A monoclonal antibody comprising a heavy chain comprising at least one, preferentially at least two, preferentially three, of CDR-H1, CDR-H2 and CDR-H3 of amino acid sequences SEQ ID NO:22, 23 and 24, respectively, or sequences with at least 80%, preferably 85%, 90%, 95% and 98% identity after optimal alignment with sequences SEQ ID NO:22, 23 and 24, respectively, and a light chain comprising at least one, preferentially at least two, preferentially three, of CDR-L1, CDR-L2 and CDR-L3 of amino acid sequences SEQ ID NO:25, 26 and 27, respectively, or sequences with at least 80%, preferably 85%, 90%, 95% and 98% identity after optimal alignment with sequences SEQ ID NO:25, 26 and 27, respectively, A monoclonal antibody comprising a heavy chain comprising at least one, preferentially at least two, preferentially at least three, of CDR-H1, CDR-H2 and CDR-H3 of amino acid sequences SEQ ID NO:28, 29 and 30, respectively, or sequences with at least 80%, preferably 85%, 90%, 95% and 98% identity after optimal alignment with sequences SEQ ID NO:28, 29 and 30, respectively, and a light chain comprising at least one, preferentially at least two, preferentially three, of CDR-L1, CDR-L2 and CDR-L3 of amino acid sequences SEQ ID NO:31, 32 and 33, respectively, or sequences with at least 80%, preferably 85%, 90%, 95% and 98% identity after optimal alignment with sequences SEQ ID NO:31, 32 and 33, respectively, and A monoclonal antibody comprising a heavy chain comprising at least one, preferentially at least two, preferentially three, of CDR-H1, CDR-H2 and CDR-H3 of amino acid sequences SEQ ID NO:34, 35 and 36, respectively, or sequences with at least 80%, preferably 85%, 90%, 95% and 98% identity after optimal alignment with sequences SEQ ID NO:34, 35 and 36, respectively, and a light chain comprising at least one, preferentially at least two, preferentially three, of CDR-L1, CDR-L2 and CDR-L3 of amino acid sequences SEQ ID NO:37, 38 and 39, respectively, or sequences with at least 80%, preferably 85%, 90%, 95% and 98% identity after optimal alignment with sequences SEQ ID NO:37, 38 and 39, respectively.

In the sense of the present invention, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of methods known by a man skilled in the art.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

In a more particular embodiment, said antibody is a monoclonal antibody selected in the group consisting of:

A monoclonal antibody comprising a heavy chain of amino acid sequence SEQ ID NO:41 and a light chain of amino acid sequence SEQ ID NO:42;

A monoclonal antibody comprising a heavy chain of amino acid sequence SEQ ID NO:43 and a light chain of amino acid sequence SEQ ID NO:44;

A monoclonal antibody comprising a heavy chain of amino acid sequence SEQ ID NO:45 and a light chain of amino acid sequence SEQ ID NO:46;

A monoclonal antibody comprising a heavy chain of amino acid sequence SEQ ID NO:47 and a light chain of amino acid sequence SEQ ID NO:48;

A monoclonal antibody comprising a heavy chain of amino acid sequence SEQ ID NO:49 and a light chain of amino acid sequence SEQ ID NO:50; and A monoclonal antibody comprising a heavy chain of amino acid sequence SEQ ID NO:51 and a light chain of amino acid sequence SEQ ID NO:52.

In another particular embodiment, the antibody used in the method of the invention is a humanised antibody.

As used herein, the expression "humanized antibody" means an antibody that contains CDR regions derived from an antibody of nonhuman origin, the other parts of the antibody molecule being derived from one or several human antibodies. In addition, some of the skeleton segment residues (called FR for framework) can be modified to preserve binding affinity, according to techniques known by a man skilled in the art (Jones et al., Nature, 321:522-525, 1986). The goal of humanisation is a reduction in the immunogenicity of a xenogenic antibody, such as a murine antibody, for introduction into a human, while maintaining the full antigen binding affinity and specificity of the antibody.

The humanized antibodies of the invention or fragments of same can be prepared by techniques known to a person skilled in the art (such as, for example, those described in the documents Singer et al., J. Immun., 150:2844-2857, 1992). Such humanized antibodies are preferred for their use in methods involving in vitro diagnoses or preventive and/or therapeutic treatment in vivo. Other humanization techniques are also known to the person skilled in the art. Indeed, Antibodies can be humanized using a variety of techniques including CDR-grafting (EP 0 451 261; EP 0 682 040; EP 0 939 127; EP 0 566 647; U.S. Pat. Nos. 5,530,101; 6,180,370; 5,585,089; 5,693,761; 5,639,641; 6,054,297; 5,886,152; and 5,877,293), veneering or resurfacing (EP 0 592 106; EP 0 519 596; Padlan E. A., 1991, Molecular Immunology 28(4/5): 489-498; Studnicka G. M. et al., 1994, Protein Engineering 7(6): 805-814; Roguska M. A. et al., 1994, Proc. Natl. Acad. Sci. U.S.A., 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741.

In a more particular embodiment, said antibody is a humanized antibody selected in the group consisting of:

A humanized antibody comprising a heavy chain comprising at least one, preferentially at least two, preferentially three, of CDR-H1, CDR-H2 and CDR-H3 of amino acid sequences SEQ ID NO:4, 5 and 6, respectively, or sequences with at least 80%, preferably 85%, 90%, 95% and 98% identity after optimal alignment with sequences SEQ ID NO:4, 5 and 6, respectively, and a light chain comprising at least one, preferentially at least two, preferentially three, of CDR-L1, CDR-L2 and CDR-L3 of amino acid sequences SEQ ID NO:7, 8 and 9, respectively, or sequences with at least 80%, preferably 85%, 90%, 95% and 98% identity after optimal alignment with sequences SEQ ID NO:7, 8 and 9, respectively, A humanized antibody comprising a heavy chain comprising at least one, preferentially at least two, preferentially three, of CDR-H1, CDR-H2 and CDR-H3 of amino acid sequences SEQ ID NO:10, 11 and 12, respectively, or sequences with at least 80%, preferably 85%, 90%, 95% and 98% identity after optimal alignment with sequences SEQ ID NO:10, 11 and 12, respectively, and a light chain comprising at least one, preferentially at least two, preferentially three, of CDR-L1, CDR-L2 and CDR-L3 of amino acid sequences SEQ ID NO:13, 14 and 15, respectively, or sequences with at least 80%, preferably 85%, 90%, 95% and 98% identity after optimal alignment with sequences SEQ ID NO:13, 14 and 15, respectively, A humanized antibody comprising a heavy chain comprising at least one, preferentially at least two, preferentially three, of CDR-H1, CDR-H2 and CDR-H3 of amino acid sequences SEQ ID NO:16, 17 and 18, respectively, or sequences with at least 80%, preferably 85%, 90%, 95% and 98% identity after optimal alignment with sequences SEQ ID NO:16, 17 and 18, respectively, and a light chain comprising at least one, preferentially at least two, preferentially three, of CDR-L1, CDR-L2 and CDR-L3 of amino acid sequences SEQ ID NO:19, 20 and 21, respectively, or sequences with at least 80%, preferably 85%, 90%, 95% and 98% identity after optimal alignment with sequences SEQ ID NO:19, 20 and 21, respectively, A humanized antibody comprising a heavy chain comprising at least one, preferentially at least two, preferentially three, of CDR-H1, CDR-H2 and CDR-H3 of amino acid sequences SEQ ID NO:22, 23 and 24, respectively, or sequences with at least 80%, preferably 85%, 90%, 95% and 98% identity after optimal alignment with sequences SEQ ID NO:22, 23 and 24, respectively, and a light chain comprising at least one, preferentially at least two, preferentially three, of CDR-L1, CDR-L2 and CDR-L3 of amino acid sequences SEQ ID NO:25, 26 and 27, respectively, or sequences with at least 80%, preferably 85%, 90%, 95% and 98% identity after optimal alignment with sequences SEQ ID NO:25, 26 and 27, respectively, A humanized antibody comprising a heavy chain comprising at least one, preferentially at least two, preferentially three, of CDR-H1, CDR-H2 and CDR-H3 of amino acid sequences SEQ ID NO:28, 29 and 30, respectively, or sequences with at least 80%, preferably 85%, 90%, 95% and 98% identity after optimal alignment with sequences SEQ ID NO:28, 29 and 30, respectively, and a light chain comprising at least one, preferentially at least two, preferentially three, of CDR-L1, CDR-L2 and CDR-L3 of amino acid sequences SEQ ID NO:31, 32 and 33, respectively, or sequences with at least 80%, preferably 85%, 90%, 95% and 98% identity after optimal alignment with sequences SEQ ID NO:31, 32 and 33, respectively, and A humanized antibody comprising a heavy chain comprising at least one, preferentially at least two, preferentially three, of CDR-H1, CDR-H2 and CDR-H3 of amino acid sequences SEQ ID NO:34, 35 and 36, respectively, or sequences with at least 80%, preferably 85%, 90%, 95% and 98% identity after optimal alignment with sequences SEQ ID NO:34, 35 and 36, respectively, and a light chain comprising at least one, preferentially at least two, preferentially three, of CDR-L1, CDR-L2 and CDR-L3 of amino acid sequences SEQ ID NO:37, 38 and 39, respectively, or sequences with at least 80%, preferably 85%, 90%, 95% and 98% identity after optimal alignment with sequences SEQ ID NO:37, 38 and 39, respectively, wherein said antibody also comprises constant regions of the light-chain and the heavy-chain derived from a human antibody.

In another more particular embodiment, said antibody is a humanized antibody selected in the group consisting of:
A humanized antibody comprising a heavy chain variable region of amino acid sequence SEQ ID NO:53, and a light chain variable region of amino acid sequence SEQ ID NO:54;
A humanized antibody comprising a heavy chain variable region of amino acid sequence SEQ ID NO:55, and a light chain variable region of amino acid sequence SEQ ID NO:56;
A humanized antibody comprising a heavy chain variable region of amino acid sequence selected between SEQ ID NO:57, 58, and 59, and a light chain variable region of amino acid sequence selected between SEQ ID NO:60, 61, and 62;
A humanized antibody comprising a heavy chain variable region of amino acid sequence selected between SEQ ID NO:63, 64, and 65, and a light chain variable region of amino acid sequence selected between SEQ ID NO:66, 67, and 68;
A humanized antibody comprising a heavy chain variable region of amino acid sequence selected between SEQ ID NO:69 and 71, and a light chain variable region of amino acid sequence selected between SEQ ID NO:70 and 72; and
A humanized antibody comprising a heavy chain variable region of amino acid sequence selected between SEQ ID NO:75 and 76, and a light chain variable region of amino acid sequence selected between SEQ ID NO:77 and 78;
wherein said antibody also comprises constant regions of the light-chain and the heavy-chain derived from a human antibody.

More preferably, said antibody comprises a heavy chain variable region of amino acid sequence SEQ ID NO:71 and a light chain variable region of amino acid sequence SEQ ID NO:72, said antibody also comprising constant regions of the light-chain and the heavy-chain derived from a human antibody.

Even more preferably, said antibody comprises a heavy chain of amino acid sequence SEQ ID NO:73 and a light chain of amino acid sequence SEQ ID NO:74.

In another aspect, the invention also provides immunoconjugates (interchangeably referred to as "antibody-drug conjugates," or "ADCs") comprising an progastrin-binding antibody as described herein, said antibody being conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) Curr. Opinion in Pharmacology 5:543-549; Wu et al (2005) Nature Biotechnology 23(9): 1137-1146; Payne, G. (2003) i 3:207-212; Syrigos and Epenetos (1999) Anticancer Research 19:605-614; Niculescu-Duvaz and Springer (1997) Adv. Drug Deliv. Rev. 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al, Lancet (Mar. 15, 1986) pp. 603-05; Thorpe (1985) "Antibody Carriers Of Cytotoxic Agents In Cancer Therapy: A Review," in Monoclonal Antibodies '84: Biological And Clinical Applications (A. Pinchera et al., eds) pp. 475-506. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) J. Nat. Cancer Inst. 92(19): 1573-1581; Mandler et al (2000) Bioorganic Et Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et ah, Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC 1065, and the derivatives of these toxins that have toxin activity, are also contemplated herein.

The immunoconjugate of the invention may further comprise a linker.

"Linker", "Linker Unit", or "link" means a chemical moiety comprising a covalent bond or a chain of atoms that covalently attaches a binding protein to at least one cytotoxic agent.

Linkers may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cyctotoxic agents to the addressing system. Other cross-linker reagents may be BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMP B, and SVSB (succinimidyl-(4-vinylsulfone)benzoate) which are commercially available (e.g., from Pierce Biotechnology, Inc., Rockford, Ill., U.S.A).

The linker may be a "non-cleavable" or "cleavable".

In another aspect, the invention provides a composition for use in the prevention or the treatment of lung cancer, said composition comprising an antibody recognizing an epitope including an amino acid sequence corresponding to an amino acid sequence of progastrin.

In a more specific embodiment, said composition for use in the prevention or the treatment of lung cancer comprises an antibody recognizing an epitope of progastrin wherein said epitope includes an amino acid sequence corresponding to an amino acid sequence of the N-terminal part of progastrin, wherein said amino acid sequence may include residues 10 to 14 of hPG, residues 9 to 14 of hPG, residues 4 to 10 of hPG, residues 2 to 10 of hPG or residues 2 to 14 of hPG, wherein the amino acid sequence of hPG is SEQ ID NO:1.

In a more specific embodiment, the composition for use in the prevention or the treatment of lung cancer comprises an antibody recognizing an epitope of progastrin wherein said epitope includes an amino acid sequence corresponding to an amino acid sequence of the C-terminal part of progastrin, wherein said amino acid sequence may include residues 71 to 74 of hPG, residues 69 to 73 of hPG, residues 71 to 80 of hPG (SEQ ID NO:40), residues 76 to 80 of hPG, or residues 67 to 74 of hPG, wherein the amino acid sequence of hPG is SEQ ID NO:1.

In a more particular embodiment, the composition for use in the prevention or the treatment of lung cancer comprises a progastrin-binding antibody, or an antigen-binding fragment thereof which has an affinity for progastrin of at least 5000 nM, at least 500 nM, 100 nM, 80 nM, 60 nM, 50 nM, 40 nM, 30 nM, 20 nM, 10 nM, 7 nM, 5 nM, 4 nM, 3 nM, 2 nM, 1 nM, 0.5 nM, 0.1 nM, 50 pM, 10 pM, 5 pM, 1 pM, or at least 0.1 pM, as determined by a method such as above-described.

In an even more particular embodiment, the composition for use in the prevention or the treatment of lung cancer comprises a progastrin-binding antibody, wherein said progastrin-binding molecule, or an antigen-binding fragment thereof, is a neutralizing antibody.

In another particular embodiment, a composition for use in the prevention or the treatment of lung cancer comprises a progastrin-binding antibody, wherein said progastrin-binding molecule, or an antigen-binding fragment thereof, is a humanized antibody.

In a particular embodiment, a composition for use in the prevention or the treatment of lung cancer comprises a progastrin-binding antibody, wherein said progastrin-binding molecule, or an antigen-binding fragment thereof, is conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate), as described above.

In another particular embodiment, a composition for use in the prevention or the treatment of lung cancer for a patient comprises a progastrin-binding antibody, wherein said patient has been diagnosed with lung cancer, wherein a concentration of progastrin is higher in a biological sample from said patient than in a reference sample. Preferably, said patient has been diagnosed with lung cancer by contacting an anti-PG antibody with a biological sample of said patient.

A "biological sample" as used herein is a sample of biological tissue or fluid that contains nucleic acids or polypeptides, e.g., of a lung cancer protein, polynucleotide or transcript. Such a sample must allow for the determination of the expression levels of progastrin. Progastrin is known to be a secreted protein. Preferred biological samples for the determination of the level of the progastrin protein thus include biological fluids. A "biological fluid" as used herein means any fluid that includes material of biological origin. Preferred biological fluids for use in the present invention include bodily fluids of an animal, e.g. a mammal, preferably a human subject. The bodily fluid may be any bodily fluid, including but not limited to blood, plasma, serum, lymph, cerebrospinal fluid (CSF), saliva, sweat and urine. Preferably, said preferred liquid biological samples include samples such as a blood sample, a plasma sample, or a serum sample. More preferably, the biological sample is a blood sample. Indeed, such a blood sample may be obtained by a completely harmless blood collection from the patient and thus allows for a non-invasive assessment of the risks that the subject will develop a tumor.

A "biological sample" as used herein also includes a solid cancer sample of the patient to be tested, when the cancer is a solid cancer. Such solid cancer sample allows the skilled person to perform any type of measurement of the level of the biomarker of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non tumor healthy tissue. The "cancer sample" should thus be limited to tumor tissue taken from the patient. Said "cancer sample" may be a biopsy sample or a sample taken from a surgical resection therapy.

A biological sample is typically obtained from a eukaryotic organism, most preferably a mammal, or a bird, reptile, or fish. Indeed, a "subject" which may be subjected to the method described herein may be any of mammalian animals including human, dog, cat, cattle, goat, pig, swine, sheep and monkey; or a bird; reptile; or fish. Preferably, a subject is a human being; a human subject may be known as a "patient".

By "obtaining a biological sample," it is herein meant to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

This sample may be obtained and if necessary prepared according to methods known to a person skilled in the art. In particular, it is well known in the art that the sample should be taken from a fasting subject.

In a more particular aspect, the present invention relates to a composition for use in the prevention or the treatment of lung cancer according to the invention, wherein said progastrin-binding antibody, or an antigen-binding fragment thereof, is selected among N-terminal anti-progastrin antibodies and C-terminal anti-progastrin antibodies.

Antibody compositions for use in the methods of the invention can be prepared as different formulations, including, but not limited to, an aqueous suspension, for administration by a variety of routes, including, but not limited to, parenteral, intrathecal, subcutaneous, intravenous, intramuscular, intraperitoneal, infusion or bolus administration. In some embodiments, the composition is formulated for parenteral administration, and in some specific embodiments, intravenous injection by infusion.

In a particular embodiment, a composition for use in the prevention or the treatment of lung cancer, according to the invention, comprises an effective dose the anti-progastrin antibodies of the invention ranges from 0.001 mg/kg to about 250 mg/kg, which may be given in one administration, or over multiple, spaced administrations.

In a particular embodiment, a composition for use in the prevention or the treatment of lung cancer, according to the invention, comprises a progastrin-binding antibody, or an antigen-binding fragment thereof selected among polyclonal antibodies, monoclonal antibodies, chimeric antibodies, single chain antibodies, camelized antibodies, IgA1 antibodies, IgA2 antibodies, IgD antibodies, IgE antibodies, IgG1 antibodies, IgG2 antibodies, IgG3 antibodies, IgG4 antibodies and IgM antibodies. Preferably, said antibodies are those described above. More preferably, said antibodies are humanized antibodies.

Preferably, the present invention relates to a pharmaceutical composition comprising a composition for use in the prevention or the treatment of lung cancer according to the invention, and a pharmaceutically acceptable carrier. More specifically, the pharmaceutical composition for use in the prevention or the treatment of lung cancer according to the invention, comprises an antibody as described above and a pharmaceutically acceptable carrier.

In a more particular aspect, the present invention relates to a pharmaceutical composition comprising a composition for use in the prevention or the treatment of lung cancer according to the invention, and a pharmaceutically acceptable carrier, wherein said anti-progastrin antibody is administered at a dose from 0.001 mg/kg to 250 mg/kg, and preferably at a dose of at least 0.005 mg/kg, at least 0.01 mg/kg, at least 0.05 mg/kg, at least 0.1 mg/kg, at least 0.5 mg/kg, at least 1 mg/kg, at least 5 mg/kg, at least 10 mg/kg, at least 50 mg/kg or at least 100 mg/kg. In another aspect, the present invention relates to a kit of parts comprising a composition for use in the prevention or the treatment of lung cancer, according to the invention, and an anti-cancer therapeutic molecule.

Indeed, treatment with anti-PG monoclonal antibodies as described herein can be combined with, or adjunctive to, other therapy. Non-limiting examples of other therapy include chemotherapeutic treatment, radiation therapy, surgical resection, and antibody therapy.

In another aspect, the present invention relates to a kit of part comprising a composition for use in the prevention or the treatment of lung cancer, according to the invention, and an anti-cancer therapeutic molecule chosen among: a chemotherapeutic molecule, a targeted therapy molecule.

In a particular embodiment, the present invention relates to kits of part comprising, for the simultaneous, sequential or separate administration, a composition for the treatment of lung cancer according to the invention and a chemotherapeutic molecule. Useful chemotherapeutic molecules for this purpose, include, but are not limited to folate antagonists, purine antagonists, pyrimidine antagonists, DNA alkylating molecules, DNA cross-linking drugs, antibiotics, platinum complexes, proteasome inhibitors, mitotic spindle poisons, topoisomerase inhibitors, tyrosine kinase inhibitors, and others.

In another particular embodiment, the present invention relates to kits of part comprising, for the simultaneous, sequential or separate administration, a composition according to the invention and a composition comprising another targeted therapy molecule. Such targeted therapy molecule include, but are not limited to antibodies that target EGFR, such as cetuximab or panitumumab, antibodies that target VEGF, such as bevacizumab, antibodies that target HER2, such as trastuzumab or pertuzumab, antibodies that target PD-1 and PDL-1, such as pembrolizumab, antibodies that target CTLA-4, such as ipilimumab, small molecule drugs that target EGFR, such as erlotinib, small molecule drugs that target BRAF, such as vemurafenib or dabrafenib, a recombinant fusion protein that target VEGF, such as Aflibercept.

In another particular aspect, the present invention relates to the use of a progastrin-binding antibody, or an antigen-binding fragment thereof, for the diagnosis of lung cancer.

In another particular aspect, the present invention relates to the use of a progastrin-binding antibody, or an antigen-binding fragment thereof, for the prevention or the treatment of lung cancer.

In a more particular aspect, the present invention relates to the use of a progastrin-binding antibody, or an antigen-binding fragment thereof, for the prevention or the treatment of lung cancer for a patient, wherein the concentration of progastrin in a biological sample of said patient has been determined and is higher than the concentration of progastrin of a reference biological sample.

In another particular aspect, the invention relates to the use of a pharmaceutical composition of the invention to prevent recurrence of lung cancer. Accordingly, the present disclosure provides methods and compositions useful for treating lung cancer and preventing recurrence of lung cancer in animals, including humans. The methods of treatment involve administering to a subject diagnosed with lung cancer an amount of an antibody that specifically binds progastrin effective to provide a therapeutic benefit. The anti-PG antibody may be administered alone, as monotherapy, or in conjunction with, or adjunctive to, other treatment modalities, such as tumour resection, radiation therapy, chemotherapy, therapy with another antibody, etc.

Solid tumours are not necessarily homogenous tissues. Rather, some tumours comprise a plurality of aberrant cell types having distinct phenotypic and functional properties. In this respect, such tumours are analogous to abnormal organs. Cells comprising solid tumours differ with respect to the extent to which they are capable of initiating formation of a new tumour when transplanted to a new site in the same host, or to a new host of the same or different species. Cells having this property are known as tumour or cancer initiating cells, or alternatively, tumour or cancer stem cells. See, e.g., Hardavella et al., 2016, "Lung cancer stem cells— characteristics, phenotype," Transl Lung Cancer Res. 2016, 5(3): 272-279. Such cells are highly tumorigenic.

Generally, cancer stem cells are defined by two properties: the ability to self-renew and the ability to give rise to daughter cells that differentiate into non-stem cells. Self-renewal is the ability to undergo cell division whereby one or both daughter cells remain undifferentiated, retaining the ability to give rise to yet another cancer stem cell with similar capacity to proliferate as the parental cell. This property allows cancer stem cells to ultimately give rise to the great number cells that comprise the growing tumour. Cancer stem cells also have the ability to produce daughter cells that differentiate, giving rise to a spectrum of more differentiated non-stem, or bulk, tumour cells found in many solid tumours. Thus, when transplanted, cancer stem cells can reconstitute the type of tumour from which they originated, even after multiple, serial transplantations. Furthermore, it is thought that cancer stem cells harbour genetic mutations and/or epigenetic changes that result in altered proliferation patterns and/or low rates of apoptosis.

Cancer stem cells can be identified according to a number of phenotypic characteristics that distinguish them from bulk tumour cells. Methods useful for assessing whether a tumour or cell line contains cancer stem cells are familiar to those of skill in the art. Such methods are described for example in Hardavella et al., 2016, "Lung cancer stem cells—characteristics, phenotype," Transl Lung Cancer Res. 2016, 5(3): 272-279, as well as in WO 2012/013609. Particular instances of these methods are also described in the examples of the present application.

In a more particular aspect, the present invention relates to the use of a progastrin-binding antibody, or an antigen-binding fragment thereof, for the prevention or the treatment of lung cancer for a patient, wherein said patient presents metastasis.

In an even more particular aspect, the present invention relates to the use of a progastrin-binding antibody, or an antigen-binding fragment thereof, for the prevention or the treatment of lung cancer for a patient, wherein said patient presents metastasis and wherein the concentration of progastrin in a biological sample of said patient has been determined and is higher than the concentration of progastrin of a reference biological sample.

The constituents of which the combination is composed may be administered simultaneously, separately, or sequentially so as to obtain the maximum efficacy of the combination; it being possible for each administration to vary in its duration from a rapid administration to a continuous perfusion.

As used herein, "simultaneous administration" refers to the administration of the two compounds of the composition according in a single and unique pharmaceutical form. As used herein, "separate administration" refers to the administration, at the same time, of the two compounds of the composition according to the invention in distinct pharmaceutical forms. As used herein, "sequential administration" refers to the successive administration of the two compounds of the composition according to the invention, each in a distinct pharmaceutical form.

A "therapeutically effective amount", as used herein, refers to the minimum concentration or amount of a compound (or of compounds) which is effective to prevent, alleviate, reduce or ameliorate symptoms of disease or prolong the survival of the patient being treated.

In another aspect, the present disclosure provides a method for preventing prostate cancer recurrence, comprising administering an effective amount of an anti-PG antibody to a subject in need of prevention. Methods of preventing liver cancer recurrence according to the present disclosure are accomplished by administering one or more anti-PG antibody capable of neutralizing PG, described above, to individuals at risk for lung cancer recurrence.

Subjects in need of prevention of prostate cancer recurrence are individuals previously treated for lung cancer, who are at risk of, but have not been diagnosed with lung cancer again. Suitable subjects include individuals previously treated for lung cancer by any means, including surgical resection, chemotherapy, or any other therapy.

Effective prevention of lung cancer recurrence includes, but is not limited to, a complete and ongoing absence of lung cancer recurrence. In some embodiments, effective prevention is measured by an absence of lung cancer tumours or lung cancer stem cells obtained from a subject at risk for lung cancer recurrence. In some embodiments, effective prevention is determined by a lack of increase in blood concentration of PG in a subject at risk for lung cancer recurrence.

Anti-PG treatment can be administered alone, as monotherapy, or in combination with, or adjunctive to, one or more other treatments. Other treatments include, without limitation, surgical resection, and treatment with a second therapeutic agent, such as a chemotherapeutic agent or an antibody, as described above. Combination treatment as provided herein involves the administration of at least two treatments to a patient, one of which is anti-PG treatment with at least one anti-PG antibody, and the other of which is treatment with a therapeutic agent or procedure.

The anti-PG antibody and a second agent can be administered simultaneously, successively, or separately. As used herein, the anti-PG antibody and the second agent are said to be administered successively if they are administered to the patient on the same day, for example during the same patient visit. Successive administration can occur 1, 2, 3, 4, 5, 6, 7 or 8 hours apart. In contrast, the anti-PG antibody and the second agent are said to be administered separately if they are administered to the patient on different days, for example, the anti-PG antibody and the second therapeutic agent can be administered at a 1-day, 2-day or 3-day, one-week, 2-week or monthly intervals. In the methods of the present disclosure, administration of the anti-PG antibody of the disclosure can precede or follow administration of the second agent. As a non-limiting example, the anti-PG antibody and second agent can be administered concurrently for a period of time, followed by a second period of time in which the administration of anti-PG antibody and the second agent are alternated.

The characteristics of the embodiments of the invention will become further apparent from the following detailed description of examples below.

EXAMPLES

Example 1: Neutralizing Activity of Anti-hPG Antibodies on Cancer Cell Lines 1.1. Neutralizing Activity of Anti-hPG Monoclonal Antibodies Monoclonal antibodies to PG are tested for their ability to inhibit proliferation of several cell lines commonly used to study lung cancer, which produce and secrete progastrin. Survival of cells from each of these cell lines is tested using different anti-hPG monoclonal antibodies.

For each experiment, 50,000 cells are seeded into 6-well plates in medium containing fetal calf serum and incubated for 8 hours. Cells are serum-starved overnight, and starting at 24 hours after seeding (time "T0"), cells are treated in sextuplicates every 12 h for 48 hours, in the absence of fetal calf serum, with 1 to 20 µg/ml of monoclonal control antibodies (monoclonal antibody anti-puromycin)(CT mAb), or with 1 to 20 µg/ml anti-hPG mAb, wherein said mAb is a C-terminal anti-hPG monoclonal antibody or a N-terminal anti-hPG monoclonal antibody.

Said mAb is a C-terminal anti-hPG antibody, selected among:

An antibody comprising a heavy chain comprising CDR-H1, CDR-H2 and CDR-H3 of amino acid sequences SEQ ID NO:28, 29 and 30, and a light chain comprising CDR-L1, CDR-L2 and CDR-L3 of amino acid sequences SEQ ID NO:31, 32 and 33, An antibody comprising a heavy chain comprising CDR-H1, CDR-H2 and CDR-H3 of amino acid sequences SEQ ID NO:34, 35 and 36, and a light chain comprising CDR-L1, CDR-L2 and CDR-L3 of amino acid sequences SEQ ID NO:37, 38 and 39.

or a N-terminal anti-hPG antibody selected among:

An monoclonal antibody comprising a heavy chain comprising CDR-H1, CDR-H2 and CDR-H3 of amino acid sequences SEQ ID NO:4, 5 and 6, respectively, and a light chain comprising CDR-L1, CDR-L2 and CDR-L3 of amino acid sequences SEQ ID NO:7, 8 and 9, An antibody comprising a heavy chain comprising CDR-H1, CDR-H2 and CDR-H3 of amino acid sequences SEQ ID NO:10, 11 and 12, respectively, and a light chain comprising CDR-L1, CDR-L2 and CDR-L3 of amino acid sequences SEQ ID NO:13, 14 and 15, respectively, An antibody comprising a heavy chain comprising CDR-H1, CDR-H2 and CDR-H3 of amino acid sequences SEQ ID NO:16, 17 and 18, respectively, and a light chain comprising CDR-L1, CDR-L2 and CDR-L3 of amino acid sequences SEQ ID NO:19, 20 and 21, respectively, An antibody comprising a heavy chain comprising CDR-H1, CDR-H2 and CDR-H3 of amino acid sequences SEQ ID NO:22, 23 and 24, respectively, and a light chain comprising CDR-L1, CDR-L2 and CDR-L3 of amino acid sequences SEQ ID NO:25, 26 and 27, respectively, The number of cells at T0 is counted in a control well, for each experiment.

Specifically, the number of live cells in both control and anti-hPG mAb treated wells is counted at 48 hours, then the difference between each cell count and the cell count determined at T0, is calculated. The resulting number of anti-hPG mAb-treated cells is then expressed as a percentage of the number of control mAb-treated cells.

Treatment with anti-hPG monoclonal antibodies reduces cell number as compared to treatment with control antibody. Statistical significance is determined using a one-way ANOVA with a Tukey post-hoc test: *=p<0.05, =p<0.01, and *=p<0.001. In each cell line, anti-hPG antibodies reduce cell survival.

1.2. Neutralizing Activity of Anti-hPG Humanized Antibodies on Cell Survival

Humanized antibodies to PG are tested for their ability to inhibit proliferation of several cell lines commonly used to study lung cancer, which produce and secrete progastrin. Survival of cells from each of these cell lines is tested using different anti-hPG monoclonal antibodies.

For each experiment, 50,000 cells are seeded into 6-well plates in medium containing fetal calf serum and incubated for 8 hours. Cells are serum-starved overnight, and starting at 24 hours after seeding (time "T0"), cells are treated in sextuplicates every 12 h for 48 hours, in the absence of fetal calf serum, with 1 to 20 Ng/ml of humanized control antibodies (anti-human FcG1, from BioXCell)(CT Hz), or with 1 to 20 µg/ml anti-hPG Hz, wherein said Hz is a C-terminal anti-hPG humanized antibody or a N-terminal anti-hPG humanized antibody. The number of cells at T0 is counted in a control well, for each experiment.

Specifically, the number of live cells in both control and anti-hPG Hz treated wells is counted at 48 hours, then the difference between each cell count and the cell count determined at T0, is calculated. The resulting number of anti-hPG Hz-treated cells is then expressed as a percentage of the number of control mAb-treated cells.

Treatment with anti-hPG Hz antibodies reduces cell number as compared to treatment with control antibody. Statistical significance is determined using a one-way ANOVA with a Tukey post-hoc test: *=p<0.05, =p<0.01, and *=p<0.001. In each cell line, anti-hPG antibodies reduce cell survival.

1.3. Neutralizing Activity of Anti-hPG Monoclonal Antibodies on Cancer Stem Cell Frequency Monoclonal antibodies to PG are tested for their ability to reduce cancer stem cell (CSC) frequency using Extreme Limiting Dilution Assay (ELDA), in several cell lines commonly used to study lung cancer, which produce and secrete progastrin. CSC frequency from each of these cell lines is tested using different anti-hPG monoclonal antibodies.

For each experiment, cells are seeded in ultra-low attachment (ULA) P96 (96-well plates) at fixed cellular concentrations per well using a FACS Aria flow cytometer, and a range of concentrations is used from one to 500 cells per well. The cells are cultivated for up to 11 days in ULA plates with M11 medium (Macari et al, Oncogene, 2015) and treated every 3 or 4 days with 1 to 20 µg/ml of monoclonal control antibodies (monoclonal antibody anti-puromycin) (CT mAb), or with 1 to 20 µg/ml anti-hPG mAb, wherein said mAb is a C-terminal anti-hPG monoclonal antibody or a N-terminal anti-hPG monoclonal antibody.

Specifically, at the end of the incubation phase, the plates are observed with a phase-contrast microscope and the number of positive wells per cellular concentration is assessed. Finally, the ELDA webtool (http://www.bioinf.wehi.edu.au/software/elda/) is used to calculate the CSC frequencies of each treatment group and test for any statistical difference between groups (modified Chi-square test).

Treatment with anti-hPG monoclonal antibodies reduces CSC frequency as compared to treatment with control antibody.

1.4. Neutralizing Activity of Anti-hPG Humanized Antibodies on Cancer Stem Cell Frequency Sphere Formation Assay Humanized antibodies to PG are tested for their ability to reduce cancer stem cell (CSC) frequency using sphere formation assay in several cell lines commonly used to study lung cancer, which produce and secrete progastrin.

For each experiment, 700 cells are seeded in 24-well ultra-low attachment (ULA). The cells are cultivated for up to 7 days in ULA plates with M11 medium (Macari et al, Oncogene, 2015) and treated every 3 or 4 days with 20 µg/ml of humanized control antibodies (anti-human FcG1, from BioXCell)(CT Hz), or with 20 µg/ml anti-hPG Hz (PG Hz), wherein said Hz is a C-terminal anti-hPG humanized antibody or a N-terminal anti-hPG humanized antibody.

Specifically, at the end of the incubation phase, the wells are photographed via brightfield microscopy, the pictures are analyzed and the spheres with a mean diameter above 25 µm are counted.

Treatment with anti-hPG humanized antibodies reduces CSC frequency as compared to treatment with control antibody.

Extreme Limiting Dilution Assay

Humanized antibodies to PG are tested for their ability to reduce cancer stem cell (CSC) frequency using Extreme Limiting Dilution Assay (ELDA) in several cell lines commonly used to study lung cancer, which produce and secrete progastrin. CSC frequency from each of these cell lines is tested using different anti-hPG humanized antibodies.

For each experiment, cells are seeded in ultra-low attachment (ULA) P96 (96-well plates) at fixed cellular concentrations per well using a FACS Aria flow cytometer, and a range of concentrations is used from one to 500 cells per well. The cells are cultivated for up to 11 days in ULA plates with M11 medium (Macari et al, Oncogene, 2015) and treated every 3 or 4 days with 1 to 20 µg/ml of humanized control antibodies (anti-human FcG1, from BioXCell)(CT Hz), or with 1 to 20 µg/ml anti-hPG Hz, wherein said Hz is a C-terminal anti-hPG humanized antibody or a N-terminal anti-hPG humanized antibody.

Specifically, at the end of the incubation phase, the plates are observed with a phase-contrast microscope and the number of positive wells per cellular concentration is assessed. Finally, the ELDA webtool (http://www.bioinf.wehi.edu.au/software/elda/) is used to calculate the CSC frequencies of each treatment group and test for any statistical difference between groups (modified Chi-square test).

Treatment with anti-hPG humanized antibodies reduces CSC frequency as compared to treatment with control antibody.

1.5. Neutralizing Activity of Anti-hPG Monoclonal Antibodies on the WNT/ß-Catenin Pathway Monoclonal antibodies to PG are tested for their ability to inhibit the WNT/ß-catenin pathway in several cell lines commonly used to study lung cancer, which produce and secrete progastrin, using the expression of the protein survivin, a well-known WNT/ß-catenin pathway targeted gene, as read-out. Survivin expression from each of these cell lines is tested using different anti-hPG monoclonal antibodies.

For each experiment, 50,000 cells are seeded into 6-well plates in medium containing fetal calf serum and incubated for 8 hours. Cells are serum-starved overnight, and starting 24 hours after seeding cells are treated in quadruplicate every 12 h for 72 hours, in the absence of fetal calf serum, with 1 to 20 µg/ml of monoclonal control antibodies (monoclonal antibody anti-puromycin)(CT mAb), or with 1 to 20 µg/ml anti-hPG mAb, wherein said mAb is a C-terminal anti-hPG monoclonal antibody or a N-terminal anti-hPG monoclonal antibody.

Specifically, after 72 hours of treatment, cells are harvested and total proteins are extracted using RIPA buffer. An equal amount of protein from CT mAb or anti-hPG mAb treated cells are then subjected to a western blot using anti-survivin antibody (monoclonal antibody, #2802 from Cell Signaling) and anti-actin antibody as loading control (monoclonal antibody, #A4700 from SIGMA). Quantification is performed using the GBOX chemi system from Syngene.

Treatment with anti-hPG monoclonal antibodies reduces survivin expression as compared to treatment with control antibody. Statistical significance is determined using a unpaired Student's T-test: *=$p<0.05$, =$p<0.01$, and *=$p<0.001$.

1.6. Neutralizing Activity of Anti-hPG Humanized Antibodies on the WNT/ß-Catenin Pathway Humanized antibodies to PG are tested for their ability to inhibit the WNT/ß-catenin pathway in several cell lines commonly used to study lung cancer, which produce and secrete progastrin, using the expression of the protein survivin, a well-known WNT/ß-catenin pathway targeted gene, as read-out. Survivin expression from each of these cell lines is tested using different anti-hPG humanized antibodies.

For each experiment, 50,000 cells are seeded into 6-well plates in medium containing fetal calf serum and incubated for 8 hours. Cells are serum-starved overnight, and starting 24 hours after seeding cells are treated in quadruplicate every 12 h for 72 hours, in the absence of fetal calf serum, with 1 to 20 µg/ml of humanized control antibodies (anti-human FcG1, from BioXCell)(CT Hz), or with 1 to 20 µg/ml anti-hPG Hz, wherein said Hz is a C-terminal anti-hPG humanized antibody or a N-terminal anti-hPG humanized antibody.

Specifically, after 72 hours of treatment, cells are harvested and total proteins are extracted using RIPA buffer. An equal amount of protein from CT Hz or anti-hPG Hz treated cells are then subjected to a western blot using anti-survivin antibody (monoclonal antibody, #2802 from Cell Signaling) and anti-actin antibody as loading control (monoclonal antibody, #A4700 from SIGMA). Quantification is performed using the GBOX chemi system from Syngene.

Treatment with anti-hPG humanized antibodies reduces survivin expression as compared to treatment with control antibody. Statistical significance is determined using a unpaired Student's T-test: *=$p<0.05$, =$p<0.01$, and *=$p<0.001$.

Example 2: Neutralizing Activity of Anti-hPG Antibodies on Cancer Cell Lines

Neutralizing Activity of Anti-hPG Humanized Antibodies on Cell Survival

Humanized antibodies to PG were tested for their ability to inhibit proliferation of several cell lines commonly used to study lung cancer (i.e., NCI-H358, A549 or NCI-H460), which produce and secrete progastrin. Survival of cells from each of these cell lines was assayed using different anti-hPG monoclonal antibodies.

200,000 NCI-H358 cells were seeded into 6-well plates in medium containing foetal calf serum and incubated for 8 hours. Cells were serum-starved overnight. From 24 hours after seeding (time "T0"), cells were treated in every 12 h for 48 hours, in the absence of foetal calf serum, with 20 µg/ml of humanized control antibodies (anti-human FcG1, from BioXCell) (CT Hz), or with 20 µg/ml anti-hPG Hz 8CV2 (PG Hz), wherein said Hz is a C-terminal anti-hPG humanized antibody. The number of cells at T0 was counted in a control well, for each experiment.

Specifically, the number of live cells in both control and anti-hPG Hz treated wells was counted at 48 hours. The difference between each cell count and the cell count determined at T0, was then calculated.

Treatment with anti-hPG Hz antibodies reduced cell number as compared to treatment with control antibody. Statistical significance was determined using a t-test: **=p<0.01, In each cell line, anti-hPG antibodies reduced cell survival (see FIG. 1).

BIBLIOGRAPHIC REFERENCES

Yanaoka et al, Cancer Epidemiol Biomarkers Prev, 2008, 17(4)

Pepe et al, J Natl Cancer Inst, 2008, October, 100(20)

Leja et al, Best Practice Et Research Clinical Gastroenterology, 2014, December, 28(6)

The invention claimed is:

1. A method of treating lung cancer, comprising administering an effective amount of a progastrin-binding antibody, or an antigen-binding fragment thereof, to a patient in need thereof,
   wherein said progastrin-binding antibody is selected from the group consisting of:
   an antibody comprising a heavy chain comprising CDR-H1, CDR-H2, and CDR-H3 of SEQ ID NO:4, SEQ ID NO:5, and SEQ ID NO:6, respectively, and a light chain comprising CDR-L1, CDR-L2, and CDR-L3 of SEQ ID NO:7, SEQ ID NO:8, and SEQ ID NO:9, respectively,
   an antibody comprising a heavy chain comprising CDR-H1, CDR-H2, and CDR-H3 of SEQ ID NO:10, SEQ ID NO:11, and SEQ ID NO:12, respectively, and a light chain comprising CDR-L1, CDR-L2, and CDR-L3 of SEQ ID NO:13, SEQ ID NO:14, and SEQ ID NO:15, respectively,
   an antibody comprising a heavy chain comprising CDR-H1, CDR-H2, and CDR-H3 of SEQ ID NO:16, SEQ ID NO:17, and SEQ ID NO:18, respectively, and a light chain comprising CDR-L1, CDR-L2, and CDR-L3 of SEQ ID NO:19, SEQ ID NO:20, and SEQ ID NO:21, respectively,
   an antibody comprising a heavy chain comprising CDR-H1, CDR-H2, and CDR-H3 of SEQ ID NO:22, SEQ ID NO:23, and SEQ ID NO:24, respectively, and a light chain comprising CDR-L1, CDR-L2, and CDR-L3 of SEQ ID NO:25, SEQ ID NO:26, and SEQ ID NO:27, respectively,
   an antibody comprising a heavy chain comprising CDR-H1, CDR-H2, and CDR-H3 of SEQ ID NO:28, SEQ ID NO:29, and SEQ ID NO:30, respectively, and a light chain comprising CDR-L1, CDR-L2, and CDR-L3 of SEQ ID NO:31, SEQ ID NO:32, and SEQ ID NO:33, respectively, and an antibody comprising a heavy chain comprising CDR-H1, CDR-H2, and CDR-H3 of SEQ ID NO:34, SEQ ID NO:35, and SEQ ID NO:36, respectively, and a light chain comprising CDR-L1, CDR-L2, and CDR-L3 of SEQ ID NO:37, SEQ ID NO:38, and SEQ ID NO:39, respectively.

2. The method of claim 1, wherein said progastrin-binding antibody, or antigen-binding fragment thereof, is an antibody or antigen-binding fragment thereof selected in the group consisting of: a single chain antibody, an IgA1 antibody, an IgA2 antibody, an IgD antibody, an IgE antibody, an IgG1 antibody, an IgG2 antibody, an IgG3 antibody, an IgG4 antibody, and an IgM antibody.

3. The method of claim 1, wherein said progastrin-binding antibody is selected from the group consisting of:
a monoclonal antibody comprising a heavy chain variable region of SEQ ID NO:41 and a light chain variable region of SEQ ID NO:42;
a monoclonal antibody comprising a heavy chain variable region of SEQ ID NO:43 and a light chain variable region of SEQ ID NO:44;
a monoclonal antibody comprising a heavy chain variable region of SEQ ID NO:45 and a light chain variable region of SEQ ID NO:46;
a monoclonal antibody comprising a heavy chain variable region of SEQ ID NO:47 and a light chain variable region of SEQ ID NO:48;
a monoclonal antibody comprising a heavy chain variable region of SEQ ID NO:49 and a light chain variable region of SEQ ID NO:50; and
a monoclonal antibody comprising a heavy chain variable region of SEQ ID NO:51 and a light chain variable region of SEQ ID NO:52.

4. The method of claim 1, wherein said progastrin-binding antibody is a humanized antibody.

5. The method of claim 1, wherein said progastrin-binding antibody is selected from the group consisting of:
a humanized antibody comprising a heavy chain variable region of SEQ ID NO:53, and a light chain variable region of SEQ ID NO:54;
a humanized antibody comprising a heavy chain variable region of SEQ ID NO:55, and a light chain variable region of SEQ ID NO:56;
a humanized antibody comprising a heavy chain variable region of SEQ ID NO:57, SEQ ID NO:58, or SEQ ID NO:59, and a light chain variable region of SEQ ID NO:60, SEQ ID NO:61, or SEQ ID NO:62;
a humanized antibody comprising a heavy chain variable region of SEQ ID NO:63, SEQ ID NO:64, or SEQ ID NO:65, and a light chain variable region of SEQ ID NO:66, SEQ ID NO:67, or SEQ ID NO:68;
a humanized antibody comprising a heavy chain variable region of SEQ ID NO:69, or SEQ ID NO:71, and a light chain variable region of SEQ ID NO:70, or SEQ ID NO:72; and
a humanized antibody comprising a heavy chain variable region of SEQ ID NO:75 or SEQ ID NO:76, and a light chain variable region of SEQ ID NO:77 or SEQ ID NO:78;
wherein said progastrin-binding antibody also comprises constant regions of the light-chain and the heavy-chain derived from a human antibody.

6. The method of claim 1, wherein said progastrin-binding antibody comprises a heavy chain variable region of SEQ ID NO:71 and a light chain variable region of SEQ ID NO:72, said progastrin-binding antibody also comprising constant regions of the light-chain and the heavy-chain derived from a human antibody.

7. The method of claim 1, wherein said progastrin-binding antibody comprises a heavy chain of SEQ ID NO:73 and a light chain of SEQ ID NO:74.

8. A method of treating lung cancer, comprising administering to a subject in need thereof an effective amount of a pharmaceutical composition comprising a progastrin-binding antibody, or an antigen-binding fragment thereof, and a pharmaceutically acceptable carrier and/or an excipient,
wherein said progastrin-binding antibody is selected from the group consisting of:
an antibody comprising a heavy chain comprising CDR-H1, CDR-H2, and CDR-H3 of SEQ ID NO:4, SEQ ID NO:5, and SEQ ID NO:6, respectively, and a light chain comprising CDR-L1, CDR-L2, and CDR-L3 of SEQ ID NO:7, SEQ ID NO:8, and SEQ ID NO:9, respectively,
an antibody comprising a heavy chain comprising CDR-H1, CDR-H2, and CDR-H3 of SEQ ID NO:10, SEQ ID NO:11, and SEQ ID NO:12, respectively, and a light chain comprising CDR-L1, CDR-L2, and CDR-L3 of SEQ ID NO:13, SEQ ID NO:14, and SEQ ID NO:15, respectively,
an antibody comprising a heavy chain comprising CDR-H1, CDR-H2, and CDR-H3 of SEQ ID NO:16, SEQ ID NO:17, and SEQ ID NO:18, respectively, and a light chain comprising CDR-L1, CDR-L2, and CDR-L3 of SEQ ID NO:19, SEQ ID NO:20, and SEQ ID NO:21, respectively,
an antibody comprising a heavy chain comprising CDR-H1, CDR-H2, and CDR-H3 of SEQ ID NO:22, SEQ ID NO:23, and SEQ ID NO:24, respectively, and a light chain comprising CDR-L1, CDR-L2, and CDR-L3 of SEQ ID NO:25, SEQ ID NO:26, and SEQ ID NO:27, respectively,
an antibody comprising a heavy chain comprising CDR-H1, CDR-H2, and CDR-H3 of SEQ ID NO:28, SEQ ID NO:29, and SEQ ID NO:30, respectively, and a light chain comprising CDR-L1, CDR-L2, and CDR-L3 of SEQ ID NO:31, SEQ ID NO:32, and SEQ ID NO:33, respectively, and
an antibody comprising a heavy chain comprising CDR-H1, CDR-H2, and CDR-H3 of SEQ ID NO:34, SEQ ID NO:35, and SEQ ID NO:36, respectively, and a light chain comprising CDR-L1, CDR-L2, and CDR-L3 of SEQ ID NO:37, SEQ ID NO:38, and SEQ ID NO:39, respectively.

9. The method of claim 8, wherein said progastrin-binding antibody, or antigen-binding fragment thereof, is an antibody or antigen-binding fragment thereof selected in the group consisting of: a single chain antibody, an IgA1 antibody, an IgA2 antibody, an IgD antibody, an IgE antibody, an IgG1 antibody, an IgG2 antibody, an IgG3 antibody, an IgG4 antibody, and an IgM antibody.

10. The method of claim 8, wherein said progastrin-binding antibody is selected from the group consisting of:
a monoclonal antibody comprising a heavy chain variable region of SEQ ID NO:41 and a light chain variable region of SEQ ID NO:42;
a monoclonal antibody comprising a heavy chain variable region of SEQ ID NO:43 and a light chain variable region of SEQ ID NO:44;

a monoclonal antibody comprising a heavy chain variable region of SEQ ID NO:45 and a light chain variable region of SEQ ID NO:46;

a monoclonal antibody comprising a heavy chain variable region of SEQ ID NO:47 and a light chain variable region of SEQ ID NO:48;

a monoclonal antibody comprising a heavy chain variable region of SEQ ID NO:49 and a light chain variable region of SEQ ID NO:50; and a monoclonal antibody comprising a heavy chain variable region of SEQ ID NO:51 and a light chain variable region of SEQ ID NO:52.

11. The method of claim 8, wherein said progastrin-binding antibody is a humanized antibody.

12. The method of claim 8, wherein said progastrin-binding antibody is selected from the group consisting of:

a humanized antibody comprising a heavy chain variable region of SEQ ID NO:53, and a light chain variable region of SEQ ID NO:54;

a humanized antibody comprising a heavy chain variable region of SEQ ID NO:55, and a light chain variable region of SEQ ID NO:56;

a humanized antibody comprising a heavy chain variable region of SEQ ID NO:57, SEQ ID NO:58, or SEQ ID NO:59, and a light chain variable region of SEQ ID NO:60, SEQ ID NO:61, or SEQ ID NO:62;

a humanized antibody comprising a heavy chain variable region of SEQ ID NO:63, SEQ ID NO:64, or SEQ ID NO:65, and a light chain variable region of SEQ ID NO:66, SEQ ID NO:67, or SEQ ID NO:68;

a humanized antibody comprising a heavy chain variable region of SEQ ID NO:69, or SEQ ID NO:71, and a light chain variable region of SEQ ID NO:70, or SEQ ID NO:72; and a humanized antibody comprising a heavy chain variable region of SEQ ID NO:75 or SEQ ID NO:76, and a light chain variable region of SEQ ID NO:77 or SEQ ID NO:78;

wherein said progastrin-binding antibody also comprises constant regions of the light-chain and the heavy-chain derived from a human antibody.

13. The method of claim 8, wherein said progastrin-binding antibody comprises a heavy chain variable region of SEQ ID NO:71 and a light chain variable region of SEQ ID NO:72, said progastrin-binding antibody also comprising constant regions of the light-chain and the heavy-chain derived from a human antibody.

14. The method of claim 8, wherein said progastrin-binding antibody comprises a heavy chain of SEQ ID NO:73 and a light chain of SEQ ID NO:74.

15. The method of claim 8, said method further comprising administering a second therapeutic agent to said subject.

16. The method of claim 15, wherein said second therapeutic agent is a biological agent or a chemotherapeutic agent.

17. The method of claim 16, wherein said biological agent is an anti-EGFR monoclonal antibody or an anti-VEGF monoclonal antibody.

18. The method of claim 16, wherein said chemotherapeutic agent is selected from the group consisting of alkylating agents, anti-metabolites, anti-tumor antibiotics, mitotic inhibitors, chromatin function inhibitors, anti-angiogenesis agents, anti-estrogens, anti-androgens, and immunomodulators.

* * * * *